United States Patent
Reddy et al.

(10) Patent No.: US 8,404,841 B2
(45) Date of Patent: *Mar. 26, 2013

(54) PROCESS FOR THE PREPARATION OF STATINS AND THEIR PHARMACEUTICALLY ACCEPTABLE SALTS THEREOF

(75) Inventors: Manne Satyanarayana Reddy, Hyderabad (IN); Srinivasan Thirumalai Rajan, Hyderabad (IN); Maramreddy Sahadeva Reddy, Hyderabad (IN)

(73) Assignee: MSN Laboratories Limited, Hyderabad, Andhra Pradesh (IN)

( * ) Notice: Subject to any disclaimer, the term of this patent is extended or adjusted under 35 U.S.C. 154(b) by 634 days.

This patent is subject to a terminal disclaimer.

(21) Appl. No.: 12/531,386

(22) PCT Filed: Oct. 5, 2007

(86) PCT No.: PCT/IN2007/000459
§ 371 (c)(1),
(2), (4) Date: Sep. 15, 2009

(87) PCT Pub. No.: WO2008/044243
PCT Pub. Date: Apr. 17, 2008

(65) Prior Publication Data
US 2010/0056783 A1 Mar. 4, 2010

(30) Foreign Application Priority Data
Oct. 9, 2006 (IN) ............................ 1864/CHE/2006

(51) Int. Cl.
*C07D 239/42* (2006.01)
(52) U.S. Cl. ........................ 544/330; 544/332
(58) Field of Classification Search .................. 544/330, 544/332
See application file for complete search history.

(56) References Cited

U.S. PATENT DOCUMENTS

| | | | |
|---|---|---|---|
| 4,739,073 A | 4/1988 | Kathawala | |
| 4,970,313 A | 11/1990 | Wess et al. | |
| 4,977,279 A | 12/1990 | Wess et al. | |
| 5,260,440 A | 11/1993 | Hirai et al. | |
| 5,273,995 A | 12/1993 | Roth | |
| 5,354,772 A | 10/1994 | Kathawala | |
| 5,753,675 A | 5/1998 | Wattanasin | |
| 5,763,675 A | 6/1998 | Levin | |
| 5,856,336 A | 1/1999 | Fujikawa et al. | |
| 6,316,460 B1 | 11/2001 | Creekmore et al. | |
| 6,627,636 B2 | 9/2003 | Robl | |
| 6,835,838 B2 | 12/2004 | Chen et al. | |
| 6,841,554 B2 | 1/2005 | Taylor et al. | |
| 6,844,437 B1 | 1/2005 | Taylor et al. | |
| 6,875,867 B2 | 4/2005 | Brodfuehrer et al. | |
| 7,312,329 B2 | 12/2007 | Joshi et al. | |
| 7,371,865 B2 | 5/2008 | Acemoglu et al. | |
| 2004/0049036 A1 | 3/2004 | Taylor et al. | |
| 2004/0176401 A1 | 9/2004 | Matsushita et al. | |
| 2005/0080134 A1 | 4/2005 | Niddam-Hildesheim et al. | |
| 2005/0124639 A1 | 6/2005 | Joshi et al. | |
| 2005/0209259 A1 | 9/2005 | Huang | |
| 2006/0004200 A1 | 1/2006 | Gudipati et al. | |
| 2009/0275752 A1 | 11/2009 | Reddy et al. | |

FOREIGN PATENT DOCUMENTS

| | | |
|---|---|---|
| CN | 1821242 A | 8/2006 |
| CN | 101386592 A | 3/2009 |
| EP | 0 304 063 B1 | 11/1994 |
| EP | 1 099 694 B1 | 8/2005 |
| JP | 6041114 A | 5/1994 |
| WO | WO 95/11898 | 5/1995 |
| WO | WO 95/13283 | 5/1995 |
| WO | WO 97/19917 | 6/1997 |
| WO | WO 98/32751 | 7/1998 |
| WO | WO 99/11258 | 3/1999 |
| WO | WO 99/45003 | 9/1999 |
| WO | WO 01/60804 A1 | 8/2001 |
| WO | WO 02/09697 A1 | 2/2002 |
| WO | WO 02/092570 A1 | 11/2002 |
| WO | WO 02/094804 A1 | 11/2002 |
| WO | WO 03/006439 A1 | 1/2003 |
| WO | WO 03/016317 A1 | 2/2003 |
| WO | WO 03/045935 A1 | 6/2003 |
| WO | WO 03/070717 A1 | 8/2003 |
| WO | WO 03/097614 A2 | 11/2003 |
| WO | WO 2004/014872 A1 | 2/2004 |
| WO | WO 2004/108691 A1 | 12/2004 |

(Continued)

OTHER PUBLICATIONS

International Search Report for PCT/IN2007/000172, dated Jan. 18, 2008.
International Preliminary Report on Patentability from counterpart International Application No. PCT/IN2007/000172, dated Jun. 16, 2008.
Written Opinion of the International Preliminary Examining Authority from counterpart International Application No. PCT/IN2007/000172, dated Jan. 18, 2008.

(Continued)

*Primary Examiner* — Deepak Rao
(74) *Attorney, Agent, or Firm* — Hamilton, Brook, Smith & Reynolds, P.C.

(57) ABSTRACT

Novel process for the preparation of statins and their pharmaceutically acceptable salts thereof represented by the general formula-(1) through novel intermediate compounds of general formula-(4).

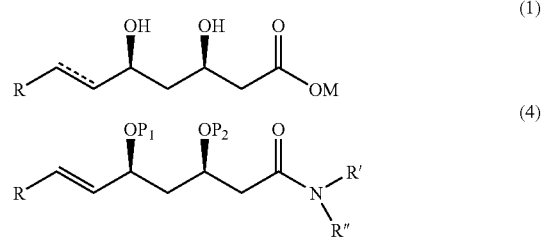

2 Claims, No Drawings

FOREIGN PATENT DOCUMENTS

| WO | WO 2005/033083 A1 | 4/2005 |
|---|---|---|
| WO | WO 2005/040134 A1 | 5/2005 |
| WO | WO 2005/042522 A1 | 5/2005 |
| WO | WO 2005/054207 A1 | 6/2005 |
| WO | WO 2005/077916 A1 | 8/2005 |
| WO | WO 2006/035277 A2 | 4/2006 |
| WO | WO 2006/079611 A1 | 8/2006 |
| WO | WO 2006/136407 A1 | 12/2006 |
| WO | WO 2007/000121 A1 | 1/2007 |
| WO | WO 2007/040940 A1 | 4/2007 |
| WO | WO 2007/041666 A1 | 4/2007 |
| WO | WO 2007/052309 A2 | 5/2007 |
| WO | WO 2007/086082 A2 | 8/2007 |
| WO | WO 2007/086082 A3 | 8/2007 |
| WO | WO 2007/100351 A2 | 9/2007 |
| WO | WO 2007/125547 A2 | 11/2007 |
| WO | WO 2007/132482 A2 | 11/2007 |
| WO | WO 2008/044243 A2 | 4/2008 |
| WO | WO 2008/044243 A3 | 4/2008 |

OTHER PUBLICATIONS

Miyachi, N., et al., "A Novel Synthetic Method of HMG-CoA Reductase Inhibitor NK-104 Via A Hydroboration-Cross Coupling Sequence", *Tetrahedron Letters*, 34(51):8267-8270 (1993).

Wess, G., et al., "Stereoselective Synthesis of HR 780 A New Highly Potent HMG-COA Reductase Inhibitor", *Tetrahedron Letters*, 31(18):2545-2548 (1990).

Takahashi, Kyoko, et al., "Synthesis of an Artificial HMG-CoA Reductase Inhibitor NK-104 via a Hydrosilylation—Cross-Coupling Reaction", *Bull. Chem. Soc. Jpn.*, 68:2649-2656 (1995).

International Preliminary Report on Patentability from counterpart International Application No. PCT/IN2007/000459, dated Aug. 4, 2010.

Written Opinion of the International Searching Authority from counterpart International Application No. PCT/IN2007/000459, dated Dec. 3, 2009.

International Search Report for International Application No. PCT/IN2007/000459, dated Dec. 3, 2009.

Author unknown, "Process for the preparation of 2, 2-dimethyl-1, 2, 3, 7, 8, 8a-hexahydro-3, 7-dimethyl-8-[2-tetrahydro-4-hydroxy-6-oxo-2H-pyran-2-yl)-ethyl]-1-napthalenyl ester and intermediates thereof", *IP.com Journal*, vol. 6(10A), 2 (No. IPCOM000140631D) compounds of formula IV (Sep. 17, 2006).

Patel, D.S., et al., "Process for preparation of 2,2-dimethylbutyric acid 8-ester of [1,2,6,7,8,8a(R)-hexahydro-2(S) ,6(R)-dimethyl-1(S)-naphthylethyl] tetrahydro-4-hydroxy-2H-pyran-2-one from broth containing [1,2,6,7,8,8a(R)-hexahydro-2(S) ,6(R)dimethyl-8(S)methyl-1-oxobutoxy-1-naphthyl]-3(R)       ,5(R)dihydroxyheptanoic acid", (abstract) Database CA [Online] Chemcial Abstracts Service Columbus, Ohio, US; Retrieved from STN International, Columbus, Ohio, USA. Accession No. 148:403004 RN 1015249-88-3 (2007).

Brousseau, M.E., et al., "Structure and mechanism of action of HMG-CoA reductase inhibitors", The British Library—"The World's Knowledge", pp. 19-34, ed. by Gerd Schmitz and Michael Torzewski, Birkhauser (2002).

International Search Report from counterpart International Application No. PCT/IN2010/000029, "Processes for Preparing Pitavas Tatin, Intermediates and Pharmaceutically Acceptable Salts Thereof", Dated Aug. 26, 2010.

Written Opinion of the International Searching Authority for International Patent Application No. PCT/IN2010/000029, "Processes for Preparing Pitavas Tatin, Intermediates and Pharmaceutically Acceptable Salts Thereof",dated Aug. 26, 2010.

International Preliminary Report on Patentability for International Application No. PCT/IN2010/000029, titled "Processes for Preparing Pitavastatin, Intermediates and Pharmaceutically Acceptable Salts Thereof", dated Jul. 19, 2011.

Cai, Zheng-yan et al., "Synthesis of Pitavastatin Calcium", *Chinese Journal of Pharmaceuticals*, 38(3): 177-180 (2007).

Johnson, Douglas S. , "The Art of Drug Synthesis", Synthesis of Pitavastatin (Livalo®), pp. 177-179, ISBN: 15978-0-471-75215-8 (2007).

PROCESS FOR THE PREPARATION OF STATINS AND THEIR PHARMACEUTICALLY ACCEPTABLE SALTS THEREOF

RELATED APPLICATION

This application claims the benefit of priority of our Indian patent provisional application No: 1864/CHE/2006, filed on 9 Oct. 2006; Also related to our co-pending International application No: PCT/IN07/000,172;

FIELD OF THE INVENTION

The present invention relates to a novel process for the preparation of statins and their pharmaceutically acceptable salts thereof represented by the general formula-1,

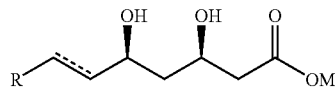

Formula-1

Wherein ⁓ denotes a single or a double bond and R is a hydrophobic anchor or a residue of HMG CoA reductase inhibitor selected from any one of the compound of formula-a to formula-g,

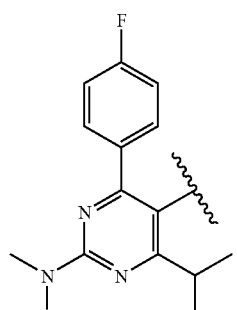

Formula-a

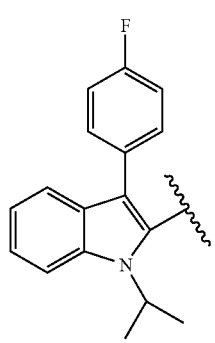

Formula-b

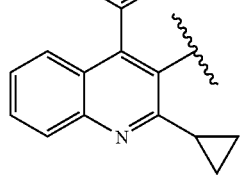

Formula-c

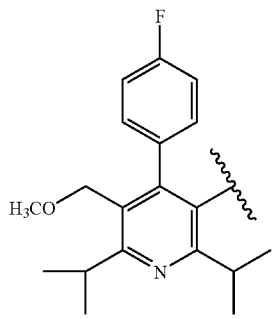

Formula-d

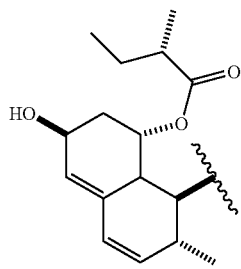

Formula-e

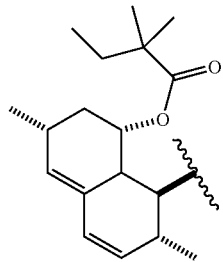

Formula-f

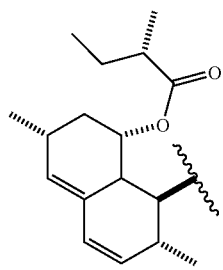

Formula-g

Wherein M is H, $Na^+$, $K^+$, $Mg^{+2}$, $Ca^{+2}$

Herein after the above compounds of formula (a), (b), (c), (d), (e), (f) and (g) are referred as 'R', The compounds of the present invention inhibit the HMG-CoA reductase, which plays a main role in the synthesis of cholesterol, and subsequently they suppress the biosynthesis of cholesterol. Therefore, they are useful in the treatment of hypercholesterolemia, hyperlipoproteinemia, and atherosclerosis.

SUMMARY OF THE INVENTION

The present invention relates to a novel process for the preparation of statins and their pharmaceutically acceptable salt compounds of general formula-1 through novel intermediates,

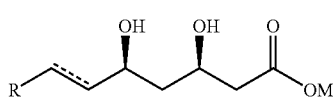

Formula-1 wherein ⸗ denotes a single or a double bond and M is H, Na⁺, K⁺, Mg⁺², Ca⁺² and R is as defined above.

Accordingly the first aspect of the present invention is to provide a novel process for the preparation of statins and their pharmaceutically acceptable salt compounds of general formula-1 through novel intermediate compounds by employing Julia-modified olefination.

The second aspect of the present invention is to provide a novel process for the preparation of statins and their pharmaceutically acceptable salt compounds of general formula-1 through novel intermediate compounds by employing Wittig-horner reaction.

The third aspect of the present invention is to provide a novel process for the preparation of statins and their pharmaceutically acceptable salt compounds of general formula-1 through novel intermediate compounds by employing Wittig reaction.

The fourth aspect of the present invention is to provide novel amide compounds of general formula-3 and process for their preparation.

The fifth aspect of the present invention is to provide novel sulfone, sulfide and sulfoxide compounds and process for their preparation.

BACKGROUND OF THE INVENTION

Rosuvastatin and its pharmaceutically acceptable salts were first disclosed in U.S. Pat. No. 5,260,440. It also discloses process for their preparation.

U.S. Pat. No. 6,875,867 disclosed a process for the preparation of HMG CoA reductase inhibitors through Julia modified-olefination reaction.

The alternate process for the preparation of rosuvastatin is disclosed in U.S. Pat. No. 6,844,437. The disclosed process involves the condensation of diphenyl[4-(4-fluorophenyl)-6-isopropyl-2-[methyl(methylsulfonyl)amino]pyrimidin-5-yl-methyl]phosphine oxide with tert-butyl-2-[(4R,6S)-6-formyl-2,2-dimethyl-1,3-dioxan-4-yl}acetate in presence of a base in a suitable solvent to provide tertiary butyl ester compound of rosuvastatin which is further converted into free acid or salt by conventional methods.

The United States patent application number US 2005/0124639 disclosed another alternate process for the preparation of rosuvastatin and its intermediates through wittig reagents. The disclosed process involves the condensation of wittig reagent like triphenyl[4-(4-fluorophenyl)-6-isopropyl-2-[methyl(methylsulfonyl)amino]pyrimidin-5-ylmethyl] phosphonium bromide or other reagent with tert-butyl-2-[(4R,6S)-6-formyl-2,2-dimethyl-1,3-dioxan-4-yl}acetate in a suitable solvent in presence of a base to provide tertiary butyl ester compound of rosuvastatin which is further converted into free acid then to calcium salt by contacting with a calcium source.

The amorphous form of rosuvastatin calcium prepared as per the disclosed process (i.e., through crystalline methyl ammonium salt) in U.S. Pat. No. 6,841,554 having the purity of more than 99.85%. The later patents like US2005/080134, WO 2005/040134 and WO 2007/086082 claim amorphous rosuvastatin calcium with high purity.

The statins are very important inhibitors of the HMG CoA reductase; hence there is a need to develop a novel cost effective process for their preparation.

Accordingly the present invention provides a novel process for the preparation of statins and their pharmaceutically acceptable salt compounds through novel intermediates which are more effective and easy to scale up in commercial batches in a convenient and cost effective manner.

BRIEF DESCRIPTION OF THE INVENTION

In accordance with the present invention, a novel process is provided for the preparation of statins and their pharmaceutically acceptable salts which are useful as anti-cholesterol agents as described hereinafter.

The first aspect of the present invention is to provide a novel process for the preparation of statins and their pharmaceutically acceptable salt compounds of general formula-1 through novel intermediates by employing Julia-modified olefination,

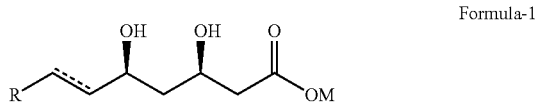

Formula-1 wherein ⸗ denotes a single or a double bond and M is H, Na⁺, K⁺, Mg⁺², Ca⁺² and R is defined as above.
which comprises of the following steps:

a) reacting the sulfone compound of general formula-2 with an amide compound of general formula-3 in presence of a suitable base in a suitable solvent to provide an olefin compound of general formula-4, b) deprotecting the alcohol or diol protecting group of olefin compound of general formula-4 by acid hydrolysis using suitable acid in a suitable solvent to provide dihydroxy compound of general formula-4x, c) reacting the dihyroxy compound of general formula-4x with a suitable base like alkali and/or alkaline metal hydroxide to provide alkali metal salt of corresponding acid compound of formula-4x followed by treating with suitable organic amine to provide corresponding organic amine salt compound of general formula-5, d) treating the organic amine salt compound of general formula-5 with a suitable acid to provide free acid compound of general formula-6, e) the alkenyl double bond in free acid compound of general formula-6 may be reduced by hydrogenation (H₂/Pd/C) to provide saturated alkyl acid compound of general formula-7, f) converting the dihydroxy compound of general formula-4x or free acid compound of general formula-6 or its organic amine compound of general formula-5 or alkyl acid compound of formula-7 into their pharmaceutically acceptable salt compounds of the general formula-1 by treating with a suitable alkali base followed by treating with alkali or alkaline earth metal salts in a suitable solvent.

The second aspect of the present invention is to provide a novel process for the preparation of statins and their pharmaceutically acceptable salt compounds of general formula-1 through novel intermediates, which comprises of the following steps:

a) reacting diphenyl phosphine oxide compound of general formula-8 with an amide compound of general formula-3 in presence of suitable base in a suitable solvent to provide olefin compound of general formula-4, b) converting the olefin compound of general formula-4 into statins or their pharmaceutically acceptable salts of general formula-1 as per the process disclosed in first aspect of the present invention.

The third aspect of the present invention is to provide a novel process for the preparation of statins and their pharmaceutically acceptable salt compounds of general formula-1 through novel intermediates by employing wittig reaction, which comprises of the following steps:

a) reacting the triphenyl phosphonium bromide compound of general formula-9 with an amide compound of general formula-3 in presence of a suitable base in a suitable solvent to provide olefin compound of general formula-4, b) converting the olefin compound of general formula-4 into statins or their pharmaceutically acceptable salts of general formula-1 as per the process disclosed in first aspect of the invention.

The fourth aspect of the present invention is to provide a novel amide intermediate compounds of general formula-3, which are useful for the preparation of HMG-CoA reductase inhibitors,

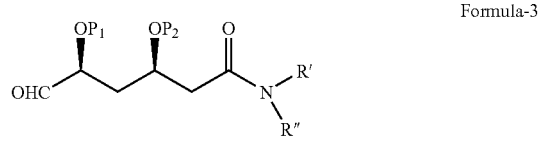

Formula-3

Wherein
$P^1$ and $P^2$ are alcohol protecting group or
$P^1$ and $P^2$, taken together to form a 1,3-diol protecting group,
R' & R" is independently selected from hydrogen, lower alkyl, alkyl, aryl or aralkyl or
R' & R" taken together with the linking nitrogen atom form a mono or bicyclic heterocycle which may optionally contain in all ring moieties further nitrogen, oxygen or sulphur heteroatoms and which may optionally be substituted.

And also provides a process for the preparation of novel amide compounds of general formula-3 useful as intermediates for the preparation of HMG-CoA reductase inhibitors, which comprises of the following steps:

a) reacting chloro hydroxy compound of formula-10 with an amide compound of general formula-11 in a suitable solvent to provide chloro hydroxy amide compound of general formula-12, b) reducing the chloro hydroxy amide compound of formula-12 selectively with a suitable reducing agent in a suitable solvent to provide dihydroxy compound of general formula-13, c) protecting the dihydroxy compound of general formula-13 by treating with a suitable alcohol or diol protecting agent in a suitable solvent to provide the protected dihydroxy compound of general formula-14, d) reacting the protected dihydroxy compound of general formula-14 with suitable acetate salt in presence of a phase transfer catalyst in a suitable solvent to provide the compound of general formula-15, e) hydrolyzing the compound of general formula-15 in presence of a suitable base in a suitable solvent to provide hydroxy amide compound of general formula-16, f) oxidizing the hydroxy amide compound of general formula-16 with a suitable oxidizing agent in presence of a catalyst in a suitable solvent to provide the amide compound of general formula-3.

The fifth aspect of the present invention is to provide an alternate process for the preparation of novel amide compounds of formula-3 useful as intermediates for the preparation of HMG-CoA reductase inhibitors, which comprises of the following steps:

a) reacting the ester compound of formula-17 with an amine compound of general formula-19 with or without presence of solvent to provide the corresponding dihydroxy compound of general formula-20, b) optionally treating the ester compound of formula-17 with suitable acid in a suitable chloro solvent to provide lactone compound of formula-18 followed by reacting with an amine compound of general formula-19 to provide the corresponding dihydroxy compound of general formula-20, c) protecting the corresponding dihydroxy compound of general formula-20 by treating with a suitable alcohol or diol protecting agent in a suitable solvent to provide the protected dihydroxy compound of general formula-16, d) oxidizing the dihydroxy amide compound of general formula-16 with a suitable oxidizing agent in presence of a catalyst in a suitable solvent to provide the amide compound of general formula-3.

The sixth aspect of the present invention is to provide a novel sulfone, sulfide and sulfoxide compounds and process for their preparation, which comprises of the following steps:

a) reacting the compound of general formula-21 with thiol compound of general formula-22 in presence of a suitable base with or without presence of a suitable solvent to provide a novel sulfide compound of general formula-23, b) oxidizing the sulfide compound of general formula-23 with an oxidizing agent in presence of an appropriate catalyst in a suitable solvent, to provide a novel sulfone compound of general formula-2 and sulfoxide compound of general formula-24 can be prepared by controlled oxidation of sulfide.

It will be appreciated that the process of the present invention may employed to prepare rosuvastatin, pravastatin, cerivastatin, fluvastatin, nisvastatin (pitavastatin), simvastatin, lovastatin and other dihydroxy acid or lactone HMG CoA reductase inhibitors.

DETAILED DESCRIPTION OF THE INVENTION

In accordance with the present invention, a novel process is provided for preparing statins (HMG-CoA reductase inhibitors) and their pharmaceutically acceptable salts which are useful as anti-cholesterol agents as described hereinafter.

The term "lower alkyl" refers to a straight or branched or cyclic $C_1$ to $C_6$ alkyl, including methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, and isohexyl and the like. Further, the lower alkyl may be substituted by 1 to 3 substituents independently selected from the group consisting of halogen, amino, hydroxy and cyano. Halogen means fluorine chlorine, bromine and iodine.

The term "alkyl" refers to straight or branched or cyclic $C_7$-$C_{12}$ alkyl

The term "aryl" refers to $C_6$-$C_{12}$ aromatic group include phenyl, tolyl, xylyl, biphenyl, naphthyl and the like. The aryl may have 1 to 3 substituents independently selected from the group consisting of lower alkyl, halogen, amino, cyano, hydroxy.

The term "aralkyl" refers to $C_1$-$C_6$ lower alkyl substituted by $C_6$-$C_{12}$ aromatic aryl group defined above. For example are benzyl, phenylethyl, phenylpropyl and the like each of which may have 1 to 3 substituents independently selected from the group consisting of lower alkyl, halogen, amino, cyano, hydroxy and the like.

The term "pharmaceutically acceptable salts" refers to the salt in which the cation is an alkali metal ion, an alkaline earth metal ion, or an ammonium ion. Examples of alkali metals are lithium, sodium, potassium and cesium, and examples of alkaline earth metals are beryllium, magnesium, and calcium. Sodium and calcium are preferred.

The term "hydrophobic anchor or residue of an HMG-CoA reductase inhibitor" employed herein denotes a "portion" or a "half" of the statin molecule, which is linked to the "other half" or "portion" i.e. dihydroxy acid or amide side chain. The "residue of HMG CoA reductase inhibitor" and the "dihydroxy acid or amide side chain" joint together to form the complete statin compound.

The term "statins" refers to the HMG-CoA reductase inhibitors like rosuvastatin, pravastatin, cerivastatin, fluvastatin, nisvastatin (pitavastatin), simvastatin, lovastatin and other dihydroxy acid HMG CoA reductase inhibitors.

The first aspect of the present invention is to provide a novel process for the preparation of statins and their pharmaceutically acceptable salt compounds of general formula-1 through novel intermediates by employing Julia-Modified olefination,

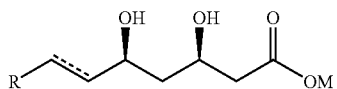

Formula-1 wherein ⟨≈⟩ denotes a single or a double bond and M is H, $Na^+$, $K^+$, $Mg^{+2}$, $Ca^{+2}$ and R is as defined above, which comprises of reacting a sulfone compound of general formula-2,

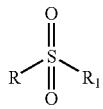

Formula-2

Wherein R is defined as above which is linked to sulphur atom with a methylene group ($-CH_2-$) and $R_1$ is

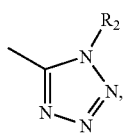

i

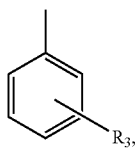

j

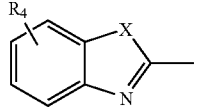

k

Wherein
$R_2$ is alkyl, aryl, arylalkyl or cycloalkyl,
$R_3$ is H, alkyl, aryl, arylalkyl, $CF_3$, halo or $NO_2$
$R_4$ is H, alkyl, alkaoxy, haloalkyl, monohaloalkyloxy, dihaloalkyloxy
And X is O, N—H, N-alkyl or S;
with an amide compound of general formula-3

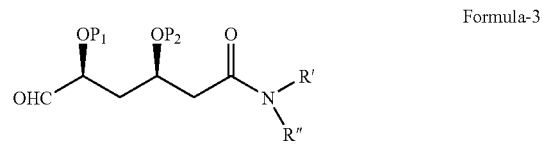

Formula-3

Wherein
$P^1$ and $P^2$ are alcohol protecting group or
$P^1$ and $P^2$, taken together to form a 1,3-diol protecting group,
R' & R" is independently selected from hydrogen, lower alkyl, alkyl, aryl or aralkyl or
R' & R" taken together with the linking nitrogen atom form a mono or bicyclic heterocycle which may optionally contain in all ring moieties further nitrogen, oxygen or sulphur heteroatoms and which may optionally be substituted.

in presence of a suitable base selected from alkali or alkaline earth metal alkoxides/hydroxides, alkali metal carbonates, amide bases, alkyl metals and metal hydrides preferably alkali metal carbonates in a suitable solvent selected from polar aprotic solvents, hydrocarbon solvents, ketone solvents, ester solvents or mixtures thereof preferably polar aprotic solvents, followed by isolation using suitable hydrocarbon solvents to provide olefin compound of general formula-4,

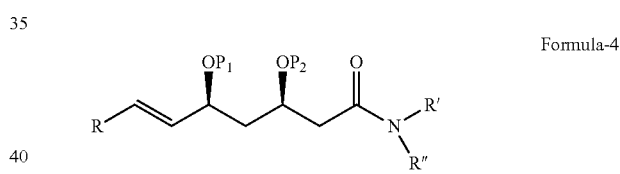

Formula-4

Deprotecting the alcohol or diol protecting group of olefin compound of general formula-4 by acid hydrolysis using suitable acids selected from hydrochloric acid, acetic acid, sulfuric acid, oxalic acid, paratoluene sulfonic acid and formic acid in a suitable solvent selected from ketone solvents, alcohol solvents, ester solvents and nitrile solvents or mixtures thereof preferably nitrile solvents, followed by isolation using suitable hydrocarbon solvents to provide dihydroxy compound of general formula-4x,

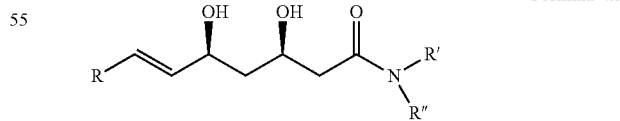

Formula-4x

Reacting the dihydroxy compound of general formula-4x with suitable base like alkali or alkali metal hydroxide in a suitable solvent like alcohol solvents, ketone solvents or mixtures thereof to provide the alkali metal salt of corresponding acid compound of formula-4x followed by treating with a suitable organic amine like tertiary butylamine, n-methyl glucamine, thiophene alkyl amine in a suitable solvent like ester solvents, nitrile solvents or mixtures thereof to provide corresponding organic amine salt compound of general formula-5,

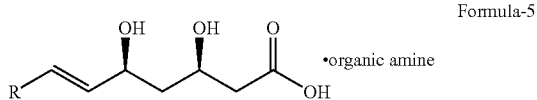

Formula-5

Treating the organic amine salt compound of general formula-5 with a suitable acid in a suitable solvent to provide free acid compound of general formula-6, The alkenyl double bond in free acid compound of general formula-6 may be reduced by hydrogenation ($H_2$/Pd/C) in a suitable solvent to provide saturated alkyl acid compound of general formula-7, Treating the organic amine salt compound of general formula-5 or dihydroxy compound of general formula-4x or alkyl acid compound of general formula-7 or free acid compound of general formula-6 with an alkali base followed by treating with alkali or alkaline earth metal salts in a suitable solvent selected from polar protic solvents, alcoholic solvents, nitrile solvents, ketone solvents or mixtures thereof preferably polar protic solvents to provide pharmaceutically acceptable salt statins compounds of general formula-1

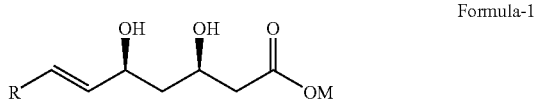

Formula-1 wherein M is H, $Na^+$, $K^+$, $Mg^{+2}$, $Ca^{+2}$.

The term "alkali metal hydroxide" refers to sodium hydroxide, potassium hydroxide and the like;

The term "alkali metal alkoxide" refers to the sodium methoxide, sodium tertiary butoxide and potassium tertiary butoxide and the like;

The term "alkali metal carbonate" refers to sodium carbonate, potassium carbonate, cesium carbonate and the like.

The term "amide bases" refers to sodium bis(trimethylsilyl)amide, potassium bis(trimethylsilyl)amide, lithium bis(trimethylsilyl) amide and the like.

The term "metal hydrides" refers to sodium hydride and potassium hydride and the like.

The term "alkyl metals" refers to butyl lithium and the like.

The term "alkaline earth metal salts" refers to calcium acetate, calcium chloride, calcium bromide and magnesium chloride and the like.

The term "polar aprotic solvents" refers to dimethylsulfoxide, dimethylacetamide, dimethyl formamide, tetrahydrofuran and the like;

The term "polar protic solvents" refers to water and the like

The term "hydrocarbon solvents" refers to toluene, xylene, cyclohexane, hexane, heptane and the like.

The term "ketone solvents" refers to acetone, methyl isobutyl ketone and the like.

The term "esters solvents" refers to ethyl acetate, methyl acetate, n-butyl acetate, isobutyl acetate, sec-butyl acetate, isopropyl acetate and the like.

The term "alcoholic solvents" refers to the methanol, ethanol, isopropanol, 2-butanol, ethylene glycol and the like.

The term "chloro solvents" refers to methylene chloride, ethylene dichloride, carbon tetra chloride, chloroform and the like.

The term "protecting agent" refers to the alcohol protecting groups such as silyl like trimethylsilyl, triethylsilyl, tertiary-butyl dimethyl silyl, triisopropylsilyl, tertiraybutyldipropyl silyl and the like; diol protecting agent such as 2,2-dialkoxy alkanes like 2,2-dimethoxy propane and the like.

The term "phase transfer catalyst" refers to the tetra-n-butylammonium bromide or methyltrioctylammonium chloride and the like.

The second aspect of the present invention is to provide a novel process for the preparation of statins and their pharmaceutically acceptable salt compounds of the general formula-1 through novel intermediate compounds,

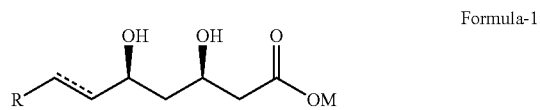

Formula-1 wherein M is H, $Na^+$, $K^+$, $Mg^{+2}$, $Ca^{+2}$ and R is as defined above which comprises of reacting the diphenyl phosphine oxide compound of general formula-8,

Formula-8

Wherein R is defined as above which is linked to phosphorus atom with a methylene group ($-CH_2-$)
With an amide compound of general formula-3

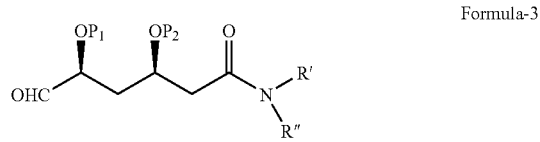

Formula-3 wherein $P_1$, $P_2$, R' & R" are defined as above
in presence of a suitable base selected from alkali or alkaline earth metal alkoxide/hydroxide, alkali metal carbonates, amide bases, alkyl metals and metal hydrides preferably amide bases in a suitable solvent selected from polar aprotic solvents, hydrocarbon solvents, ketone solvents, ester solvents or mixtures thereof preferably polar aprotic solvents, followed by isolation using suitable hydrocarbon solvents to provide olefin compound of general formula-4,

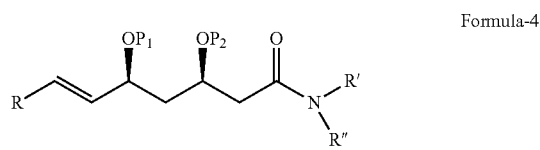

Formula-4

Deprotecting the alcohol or diol protecting group of olefin compound of general formula-4 by acid hydrolysis using suitable acids selected from hydrochloric acid, acetic acid, sulfuric acid, oxalic acid, paratoluene sulfonic acid and formic acid in a suitable solvent selected from ketone solvents, alcohol solvents, ester solvents and nitrile solvents or mixtures thereof preferably nitrile solvents, followed by isolation using suitable hydrocarbon solvents to provide dihydroxy compound of general formula-4x,

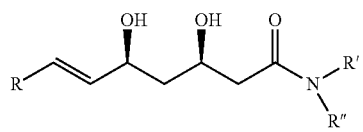

Formula-4x

Reacting the dihydroxy compound of general formula-4x with suitable base like alkali or alkali metal hydroxide in a suitable solvent like alcohol solvents, ketone solvents or mixtures thereof to provide the alkali metal salt of corresponding acid compound of formula-4x followed by treating with a suitable organic amine like tertiary butylamine, n-methyl glucamine, thiophene alkyl amine in a suitable solvent like ester solvents, nitrile solvents or mixtures thereof to provide corresponding organic amine salt compound of general formula-5,

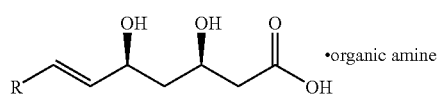

Formula-5

Treating the organic amine salt compound of general formula-5 or dihydroxy compound of general formula-4x with an alkali base followed by treating with an alkali or alkaline earth metal salts in a suitable solvent selected from polar protic solvents, alcoholic solvents, nitrile solvents, ketone solvents or mixtures thereof preferably polar protic solvents to provide pharmaceutically acceptable salt of statin compounds of general formula-1

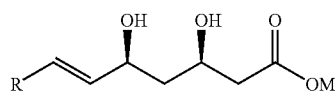

Formula-1 wherein M is H, $Na^+$, $K^+$, $Mg^{+2}$, $Ca^{+2}$.

The third aspect of the present invention is to provide a novel process for the preparation of statins and their pharmaceutically acceptable salt compounds of general formula-1 through novel intermediates by employing wittig reaction, which comprises of reacting the triphenyl phosphonium bromide compound of general formula-9,

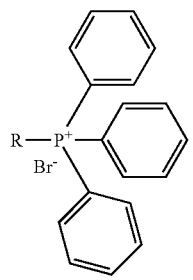

Formula-9

Wherein R is defined as above which is linked to phosphorus atom with a methylene group ($-CH_2-$)

With an amide compound of general formula-3,

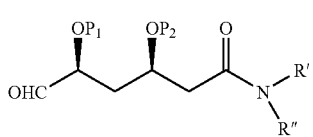

Formula-3 wherein $P_1$, $P_2$, R' & R" are defined as above
in presence of a suitable base selected from alkali or alkaline earth metal alkoxide/hydroxide, alkali metal carbonates, amide bases, alkyl metals and metal hydrides preferably alkali metal carbonates in a suitable solvent selected from polar aprotic solvents, hydrocarbon solvents, ketone solvents, ester solvents or mixtures thereof preferably polar aprotic solvents, followed by isolation using suitable hydrocarbon solvents to provide olefin compound of general formula-4,

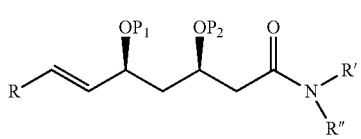

Formula-4

Deprotecting the alcohol or diol protecting group of olefin compound of general formula-4 by acid hydrolysis using suitable acids selected from hydrochloric acid, acetic acid, sulfuric acid, oxalic acid, paratoluene sulfonic acid and formic acid in a suitable solvent selected from ketone solvents, alcohol solvents, ester solvents and nitrile solvents or mixtures thereof preferably nitrile solvents, followed by isolation using suitable hydrocarbon solvents to provide dihydroxy compound of general formula-4x,

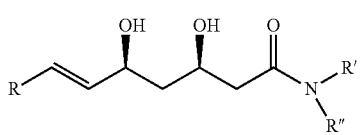

Formula-4x

Reacting the dihydroxy compound of general formula-4x with suitable base like alkali or alkali metal hydroxide in a suitable solvent like alcohol solvents, ketone solvents or mixtures thereof to provide the alkali metal salt of corresponding acid compound of formula-4x followed by treating with a suitable organic amine like tertiary butylamine, n-methyl glucamine, thiophene alkyl amine in a suitable solvent like ester solvents, nitrile solvents or mixtures thereof to provide corresponding organic amine salt compound of general formula-5,

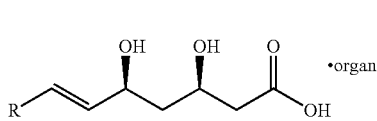

Formula-5

Treating the organic amine salt compound of general formula-5 or dihydroxy compound of general formula-4x with an alkali base followed by treating with an alkali or alkaline earth metal salts in a suitable solvent selected from polar protic solvents, alcoholic solvents, nitrile solvents, ketone solvents or mixtures thereof preferably polar protic solvents to provide pharmaceutically acceptable salt of statin compounds of general formula-1.

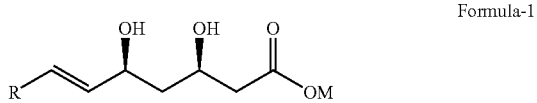

Formula-1 wherein M is H, $Na^+$, $K^+$, $Mg^{+2}$, $Ca^+$.

The fourth aspect of the present invention is to provide novel amide compounds of general formula-3 which are useful as intermediate for the preparation of statins and their pharmaceutically acceptable salt compounds of general formula-1,

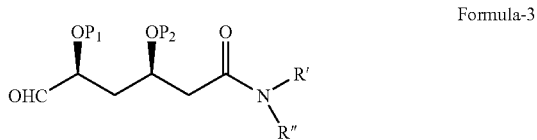

Formula-3

Wherein
$P^1$ and $P^2$ are alcohol protecting group or
$P^1$ and $P^2$, taken together to form a 1,3-diol protecting group,
R' & R" is independently selected from hydrogen, lower alkyl, alkyl, aryl or aralkyl or
R' & R" taken together with the linking nitrogen atom form a mono or bicyclic heterocycle which may optionally contain in all ring moieties further nitrogen, oxygen or sulphur heteroatoms and which may optionally be substituted.
Preferably the 1,3-diol protecting group selected from the following

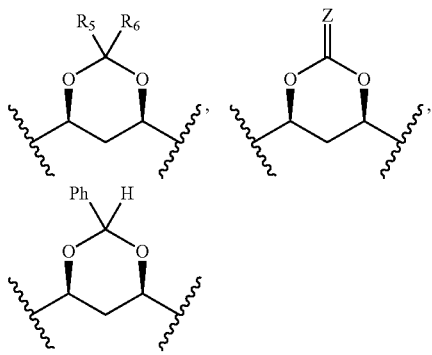

Wherein $R_5$ and $R_6$ are independently selected from $C_1$-$C_{10}$ alkyl,
Or $R_5$ and $R_6$, taken together with the carbon atom to which they are attached, form a cyclopentyl, cyclohexyl or cycloheptyl ring; and Z is an oxo or thio group The present invention also provides a process for the preparation of novel amide compounds of general formula-3 useful for the preparation of HMG-CoA reductase inhibitors, which comprises of the following steps:

a) reacting the chloro hydroxy compound of formula-10

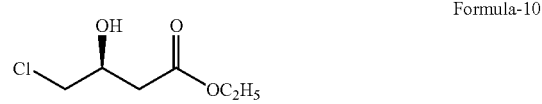

Formula-10 with an amide compound of general formula-11

Formula-11 in a suitable solvent selected from hydrocarbon solvents or polar aprotic solvents preferably polar aprotic solvents to provide the chloro hydroxy amide compound of general formula-12,

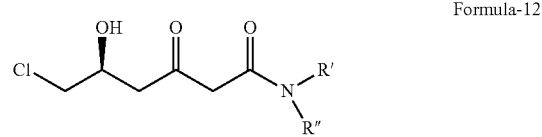

Formula-12 b) reducing the chloro hydroxy amide compound of general formula-12 selectively with a suitable reducing agent like sodiumborohydride, zinc borohydride and lithiumborohydride preferably sodiumborohydride along with borane reagent like alkyl borane, dialkyl alkoxy borane preferably dialkyl alkoxy borane like diethyl methoxy borane in a suitable polar aprotic solvent like tetrahydrofuran to provide the dihydroxy compound of general formula-13,

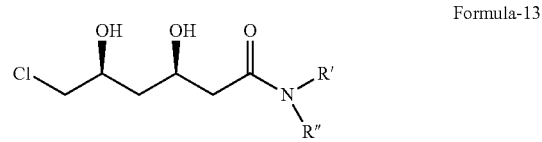

Formula-13 c) protecting the dihydroxy compound of general formula-13 by treating it with a suitable alcohol or diol protecting agent in a suitable hydrocarbon solvents or ketone solvent preferably ketone solvent like acetone to provide protected dihydroxy compound of general formula-14,

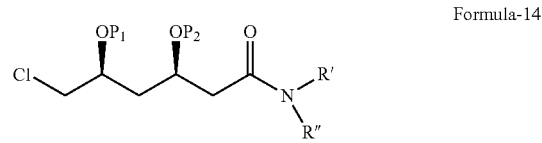

Formula-14 d) reacting the protected dihydroxy compound of general formula-14 with an acetate salt like sodium acetate in presence of a suitable phase transfer catalyst in a suitable solvent selected from ketone solvent like acetone to provide the compound of general formula-15,

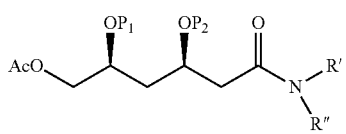
Formula-15 e) hydrolyzing the compound of general formula-15 in a suitable solvent selected from alcoholic solvents like methanol, ethanol, isopropanol, butanol preferably methanol and in presence of an alkali metal carbonate like sodium carbonate or potassium carbonate preferably potassium carbonate to provide the compound of general formula-16,

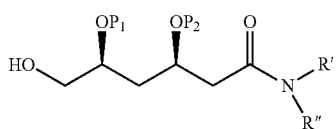
Formula-16 f) oxidizing the compound of general formula-16 with a suitable oxidizing agent like sodium hypochlorite and in presence of TEMPO (2,2,6,6-tetramethyl-1-piperidinyloxy, free radical) in a suitable solvent like acetone or in presence of oxalyl chloride and dimethyl sulfoxide to provide the amide compound of general formula-3.

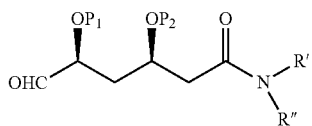
Formula-3

The present invention also provides an alternate process for the preparation of amide compounds of general formula-3 useful for the preparation of HMG-CoA reductase inhibitors, which comprises of the following steps:

a) reacting the ester compound of formula-17,

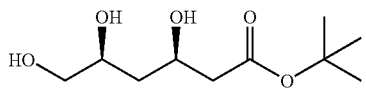
Formula-17 with an amine compound of general formula-19,

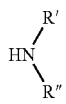
Formula-19

R' & R" are defined as above with or without the presence of a solvent to give dihydroxy amide compound of general formula-20,

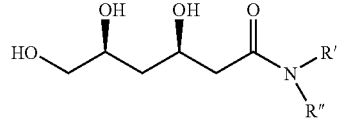
Formula-20 b) optionally treating the ester compound of formula-17 with suitable acid like trifluoroacetic acid to get the lactone compound of formula-18 followed by reacting with amine compound of general formula-19 with or without a solvent to provide the dihydroxy amide compound of general formula-20,

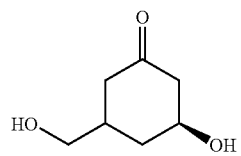
Formula-18 c) protecting the dihydroxy amide compound of formula-20 by treating with alcohol or diol protecting agent in a suitable solvent selected from ketone solvent, ester solvent, chloro solvent and hydrocarbon solvents preferably ketone solvent to provide protected dihydroxy compound of formula-16,

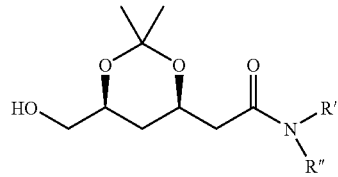
Formula-16 d) oxidizing the compound of formula-16 with a suitable oxidizing agent like sodium hypochlorite in presence of TEMPO (2,2,6,6-tetramethyl-1-piperidinyloxy, free radical) in a suitable solvent like acetone or in presence of oxalyl chloride/dimethyl sulfoxide in a suitable solvent like chloro solvents to provide the amide compound of general formula-3.

The sixth aspect of the present invention is to provide novel sulfone compounds of general formula-2, sulfoxide compounds of general formula-24, sulfide compounds of general formula-23 and process for their preparation. The present invention provides a process for the preparation of novel sulfone compound of general formula-2 and sulfoxide compound of general formula-24,

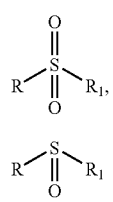
Formula-2

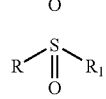
Formula-24

Wherein R is defined as above which is linked to the sulphur atom with a methylene group (—$CH_2$—) and $R_1$ is defined as above, which comprises of the following steps:

a) treating the compound of general formula-21

R—L            Formula-21

Wherein L is a leaving group such as halogen, trifluoromethanesulfonyloxy, methanesulfonyloxy, preferably halogen, more preferably bromo and R is defined as above which is linked to the leaving group with a methylene group (—CH$_2$—);

with a thiol compound of general formula-22

R$_1$SH            Formula-22 wherein R$_1$ is defined as above in presence of a suitable base like sodium hydroxide with or without presence of a suitable solvent selected from chloro solvents, ketone solvents, ester solvents, polar protic solvents or mixtures thereof, preferably keto solvents, more preferably acetone to provide a novel sulfide compound of general formula-23, Formula-23

R—S—R$_1$ wherein R is defined as above which is linked to the sulphur atom with a methylene group (—CH$_2$—) and R$_1$ is defined as above b) oxidizing a sulfide compound of general formula-23 with an oxidizing agent like metachloro per benzoic acid, sodium hypochlorite, hydrogen peroxide, tertiary butyl hydrogen peroxide, cumene hydro peroxide, preferably hydrogen peroxide in the presence of an appropriate catalyst like ammonium molybdate in a single or biphasic system in a suitable solvent selected from alcoholic solvents, chloro solvents or mixture thereof, preferably chloro solvents, more preferably methylene chloride to provide the novel sulfone compound of general formula-2 and a novel sulfoxide compound of general formula-24 can be prepared by controlled oxidation of sulfide.

According to the present invention, a preferred process is provided for the preparation of rosuvastatin calcium salt compound of formula-1a by employing Julia-modified olefination, Formula-1a Which comprises of the following steps:

Reacting the sulfone compound of formula-2a

Formula-2a with n-butyl amide compound of formula-3b

Formula-3b in presence of a suitable alkali metal carbonate like potassium carbonate in a polar aprotic solvent like dimethyl sulfoxide, followed by isolation using cyclohexane to provide corresponding olefin compound of formula-4a', Formula-4a'

Deprotecting the diol protecting group by acid hydrolysis using a suitable acid like hydrochloric acid in a suitable nitrile solvent like acetonitrile, followed by isolation using cyclohexane to provide the dihydroxy compound of formula-4-x", Formula-4x"

Treating the dihydroxy compound of formula-4-x" with an alkali base like sodium hydroxide in a suitable alcoholic solvent like ethylene glycol to provide sodium salt of corresponding acid compound of formula-4-x" followed by treating with tertiary butylamine in a suitable ester solvent like ethyl acetate, followed by isolation using nitrile solvents like acetonitrile to provide tertiary butylamine salt compound of formula-5a, Formula-5a

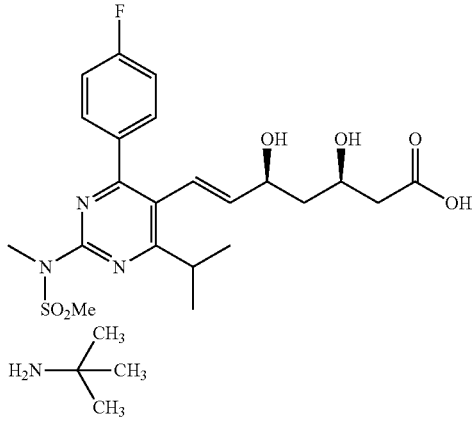

Treating the tertiary butylamine salt compound of formula-5a with an alkali base like sodium hydroxide and setting the pH of the reaction mixture to 9.1 by extracting the tertiary butylamine with tertiary butyl acetate or direct distillation followed by adding the aqueous phase of the reaction mixture to a solution of calcium chloride or calcium acetate in a suitable polar protic solvent such as water to provide the rosuvastatin calcium compound of formula-1a or treating the dihydroxy compound of formula-4-x" with alkali base like sodium hydroxide in a suitable alcoholic solvent like ethylene glycol at reflux temperature and then reacting with aqueous calcium acetate solution in a suitable polar protic solvents like water to provide rosuvastatin calcium compound of formula-1a.

According to the present invention, a preferred process is provided for the preparation of rosuvastatin calcium compound of formula-1a by employing Julia-modified olefination which comprises of the following steps:

Reacting the sulfone compound of formula-2a

Formula-2a

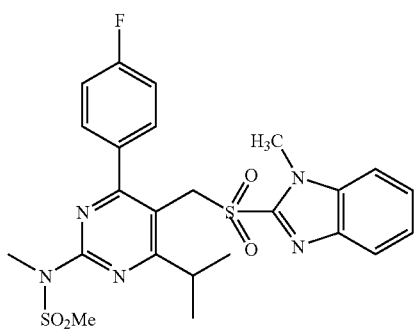

With diisopropyl amide compound of formula-3a

Formula-3a

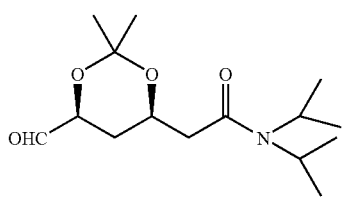

in presence of a suitable base like potassium carbonate in a polar aprotic solvent like dimethyl sulfoxide to provide olefin compound of formula-4a, Formula-4a

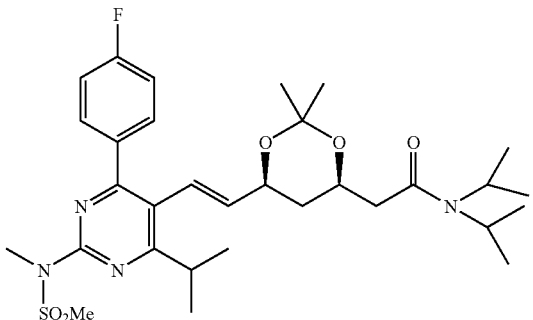

Deprotecting the diol protecting group by acid hydrolysis using a suitable acid like hydrochloric acid in a suitable nitrile solvent like acetonitrile to provide dihydroxy compound of formula-4x, Formula-4x'

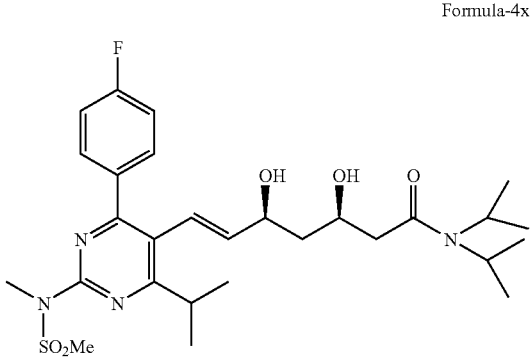

Treating the dihydroxy compound of formula-4x with an alkali base like sodium hydroxide in ethylene glycol to provide sodium salt of corresponding acid compound of formula-4x followed by treating with tertiary butylamine in ethyl acetate to provide tertiary butylamine salt compound of formula-5a, Formula-5a

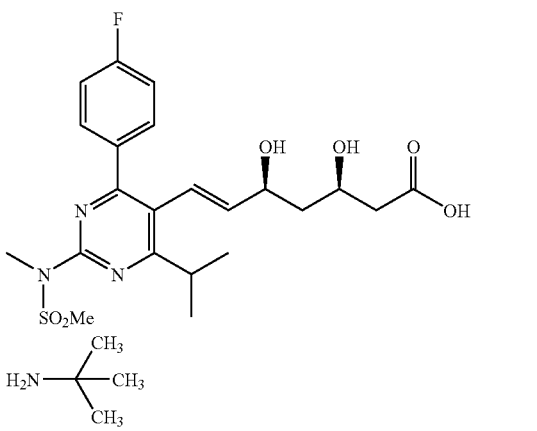

Treating the tertiary butylamine salt compound of formula-5a with an alkali base like sodium hydroxide and setting the pH of the reaction mixture to 9.1 by extracting the tertiary butylamine with tertiary butyl acetate or direct distillation followed by adding the aqueous phase of the reaction mixture to a solution of calcium chloride or calcium acetate in a suitable polar protic solvent such as water to provide rosuvastatin calcium compound of formula-1a or treating the dihydroxy compound of formula-4x with alkali base like sodium hydroxide in a suitable alcoholic solvent like ethylene glycol at reflux temperature and then reacting with aqueous calcium acetate solution in a suitable polar protic solvents like water to provide rosuvastatin calcium compound of formula-1a.

According to the present invention, a preferred process is provided for the preparation of rosuvastatin calcium compound of formula-1a, which comprises of the following steps:

Reacting the diphenyl compound of formula-8a

Formula-8a

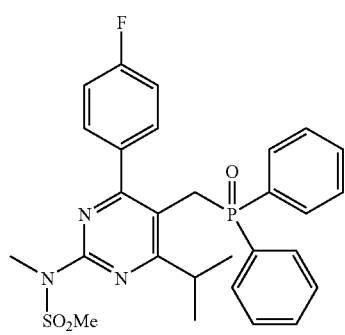

With diisopropyl amide compound of formula-3a

Formula-3a

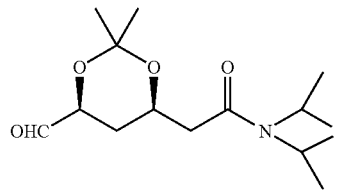

in presence of an amide base like sodium bis(trimethylsilyl) amide (NaHMDS) in polar aprotic solvent like tetrahydrofuran to provide olefin compound of formula-4a, Formula-4a

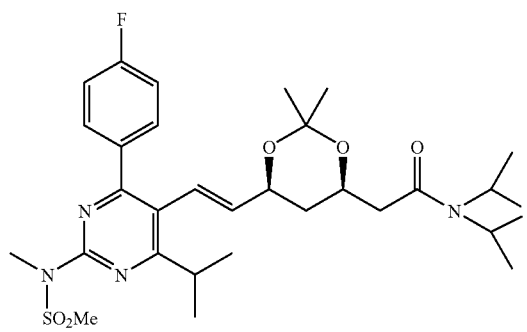

Deprotecting the diol protecting group by acid hydrolysis using a suitable acid like hydrochloric acid in a suitable nitrile solvent like acetonitrile to provide dihydroxy compound of formula-4x, Formula-4x'

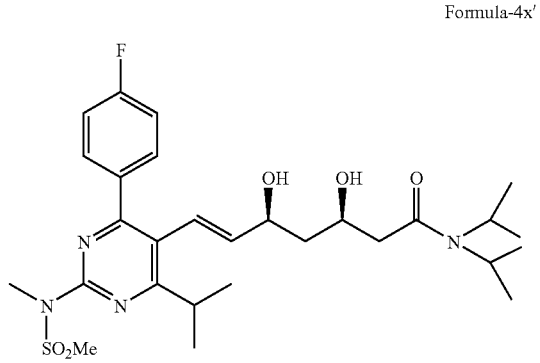 [SMILES: CC(C)c1nc(N(C)S(C)(=O)=O)nc(-c2ccc(F)cc2)c1/C=C/[C@@H](O)C[C@@H](O)CC(=O)N(C(C)C)C(C)C]

Treating the dihydroxy compound of formula-4x' with an alkali base like sodium hydroxide in ethylene glycol to provide sodium salt of corresponding acid compound of formula-4x' followed by treating with tertiary butylamine in ethyl acetate to provide tertiary butylamine salt compound of formula-5a, Formula-5a Treating the tertiary butylamine salt compound of formula-5a with an alkali base like sodium hydroxide and setting the pH of the reaction mixture to 9.1 by extracting the tertiary butylamine with tertiary butyl acetate or direct distillation followed by adding the aqueous phase of the reaction mixture to a solution of calcium chloride or calcium acetate in a suitable polar protic solvent such as water to provide rosuvastatin calcium compound of formula-1a or treating the dihydroxy compound of formula-4x with alkali base like sodium hydroxide in a suitable alcoholic solvent like ethylene glycol at reflux temperature and then reacting with aqueous calcium acetate solution in a suitable polar protic solvents like water to provide rosuvastatin calcium compound of formula-1a.

According to the present invention, a preferred process is provided for preparing rosuvastatin calcium compound of formula-1a by employing Wittig reaction, which comprises of the following steps:

Reacting the compound of formula-9a

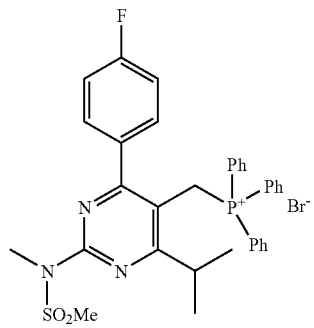

Formula-9a with n-butyl amide compound of formula-3b

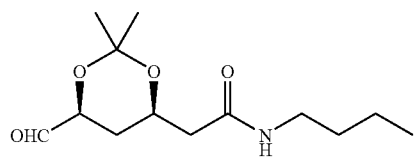

Formula-3b in presence of a suitable base like potassium carbonate in a polar aprotic solvent like dimethyl sulfoxide to provide corresponding olefin compound of or formula-4a',

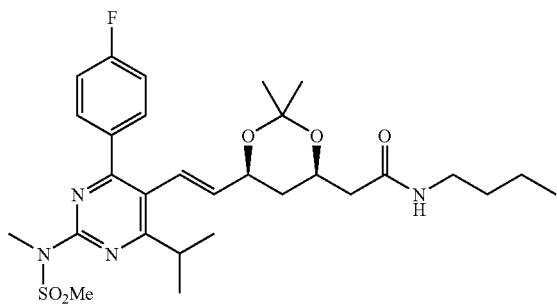

Formula-4a'

Deprotecting the diol protecting group by acid hydrolysis using a suitable acid like hydrochloride acid in a suitable nitrile solvent like acetonitrile to provide the dihydroxy compound of formula-4x",

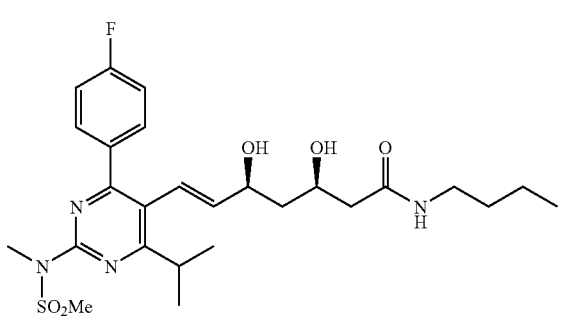

Formula-4x"

Treating the dihydroxy compound of formula-4x" with an alkali base like sodium hydroxide in a alcoholic solvents like ethylene glycol to provide sodium salt of corresponding acid compound of formula-4x" followed by treating with tertiary butylamine in a ester solvent like ethyl acetate to provide tertiary butylamine salt compound of formula-5a,

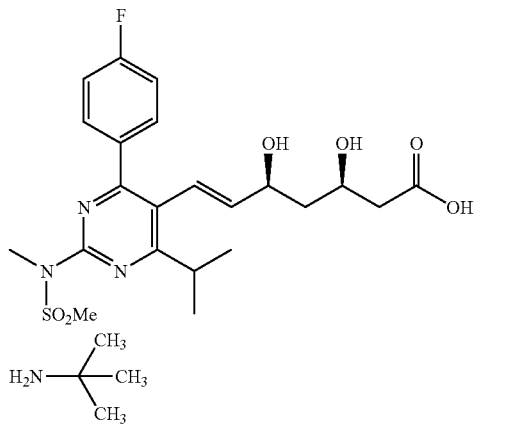

Formula-5a

Treating the tertiary butylamine salt compound of formula-5a with an alkali base like sodium hydroxide and setting the pH of the reaction mixture to 9.1 by extracting the tertiary butylamine with tertiary butyl acetate or direct distillation followed by adding the aqueous phase of the reaction mixture to a solution of calcium chloride or calcium acetate in a suitable polar protic solvent such as water to provide the rosuvastatin calcium compound of formula-1a or treating the dihydroxy compound of formula-4x" with alkali base like sodium hydroxide in a suitable alcoholic solvent like ethylene glycol at reflux temperature and then reacting with aqueous calcium acetate solution in a suitable polar protic solvent like water to provide rosuvastatin calcium compound of formula-1a.

According to the present invention, a preferred process is provided for the preparation of rosuvastatin calcium compound of formula-1a by employing Wittig reaction, which comprises of the following steps:

Reacting the compound of formula-9a

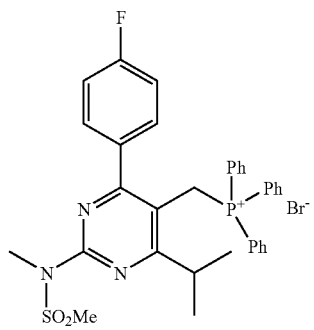

Formula-9a

With diisopropyl amide compound of formula-3a

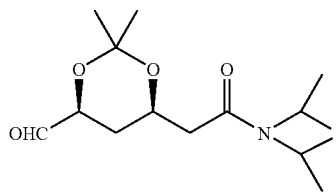

Formula-3a in presence of an alkali metal carbonates like potassium carbonate in a suitable polar aprotic solvent like dimethyl sulfoxide to provide olefin compound of formula-4a,

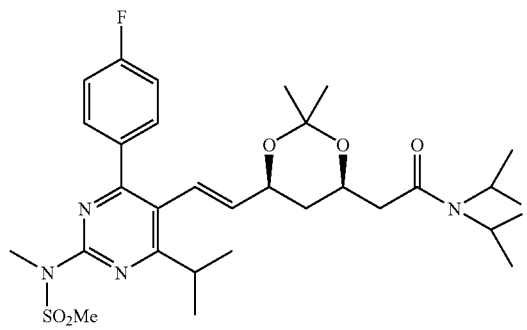

Formula-4a

Deprotecting the diol protecting group by acid hydrolysis using a suitable acid like hydrochloric acid in a suitable nitrile solvent like acetonitrile to provide dihydroxy compound of formula-4x',

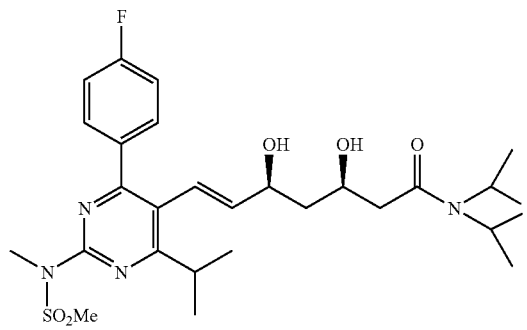

Formula-4x'

Treating the dihydroxy compound of formula-4x' with an alkali base like sodium hydroxide in ethylene glycol to provide sodium salt of corresponding acid compound of formula-4x' followed by treating with tertiary butylamine in ethyl acetate to provide tertiary butylamine salt compound of formula-5a, Formula-5a

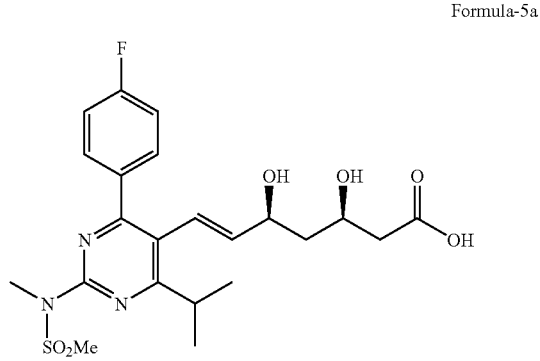

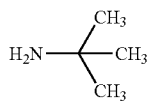

Treating the tertiary butylamine salt compound of formula-5a with an alkali base like sodium hydroxide and setting the pH of the reaction mixture to 9.1 by extracting the tertiary butylamine with tertiary butyl acetate or direct distillation followed by adding the aqueous phase of the reaction mixture to a solution of calcium chloride or calcium acetate in a suitable polar protic solvents such as water to provide rosuvastatin calcium compound of formula-1a or treating the dihydroxy compound of formula-4x' with alkali base like sodium hydroxide in a suitable alcoholic solvent like ethylene glycol at reflux temperature and then reacting with aqueous calcium acetate solution in a suitable polar protic solvents like water to provide rosuvastatin calcium compound of formula-1a.

The starting material sulfone compound of formula-2 for all statins can be prepared by the process described in our earlier Indian patent application number 805/CHE/2006 and co-pending International application number PCT/IN07/000,172.

The starting material biphenyl phosphine oxide compound of formula-8 for all statins can be prepared as per the process disclosed in the U.S. Pat. No. 6,844,437.

The starting material triphenyl phosphonium bromide salt compound of formula-9 for all statins can be prepared as per the process disclosed in the patent application number US 2005/124639.

All the stereoisomers of the compounds prepared herein are contemplated, either in admixture or in pure or substantially pure form. The compounds can have asymmetric centers at any of the carbon atoms including any one or the substitutents. Consequently, compounds of formula-1 can exist in an enantiomeric or diastereomeric forms or in mixtures thereof. The processes for preparation can utilizes racemates, enantiomers or diasteriomers as starting materials. When diasteromeric or enantiomeric products are prepared, they can be separated by conventional methods for example, chromatographic or fractional crystallization.

The particle size distribution of rosuvastatin calcium determined by laser scattering particle size distribution analyzer model Malvern Mastersizer 2000 having an accessory Scirocco 2000 using dry method technique with following specification: feed rate is 50%; air pressure is 2.0 bar; particle refractive index is 1.450; absorption is 0.1 and dispersant refractive index is 1.0

HPLC Analysis of rosuvastatin is carried out using a liquid chromatograph is equipped with variable wavelength UV-Detector or PDA-Detector having Symmetry, C18, 250×4.6 mm, 5 μm or equivalent, at a wavelength of 248 nm at ambient temperature, load is 20 μl, runtime is 70 minutes, the diluent is a mixture of water and acetonitrile in the ratio of 1:1 and the mobile phase used is a mixture of water:acetonitrile:methanol:triethylamine in the ratio of 450:250:350:1 v/v and adjusted the pH to 4.5 with glacial acetic acid.

In U.S. Pat. No. 6,316,460 discloses the degradation of the rosuvastatin under certain conditions which makes it difficult to formulate the product and provide a pharmaceutical composition with an adequate storage conditions. The major degradation product observed were lactone and ketone functionality product adjacent to carbon-carbon double bond. Hence special measures were necessary for packing and storing amorphous rosuvastatin calcium as well as pitavastatin calcium. The process for packaging and storage provide herein increased the stability of the amorphous rosuvastatin calcium and pitavastatin calcium and increased their shelf life.

A process for packing and storage of amorphous rosuvastatin calcium comprises of the following steps:
a) placing rosuvastatin calcium in a clear polyethylene bag tied with a thread,
b) placing the primary packing containing rosuvastatin calcium inside a black colour polyethylene bag and sealing it,
c) placing the above double polyethylene bag inside a triple laminated bag,
d) placing the sealed triple laminated bag inside a closed high density polyethylene (HDPE) container The oxygen busters can be used inside the black colour polyethylene bag and a triple laminated bag.

A process for packing and storage of amorphous pitavastatin calcium comprises of the following steps:
a) placing rosuvastatin calcium in a clear polyethylene bag tied with a thread,
b) placing the primary packing containing rosuvastatin calcium inside a black colour polyethylene bag and sealing it,
c) placing the above double polyethylene bag inside a triple laminated bag,
d) placing the sealed triple laminated bag inside a closed high density polyethylene (HDPE) container.

The oxygen busters can be used inside the black colour polyethylene bag and a triple laminated bag.

The bulk density and tapped density of rosuvastatin calcium were determined according to the method given in the US pharmacopeia.

The present invention schematically represented as the following schemes the invention not limited to rosuvastatin, pravastatin, cerivastatin, fluvastatin, nisvastatin (pitavastatin), simvastatin and lovastatin.

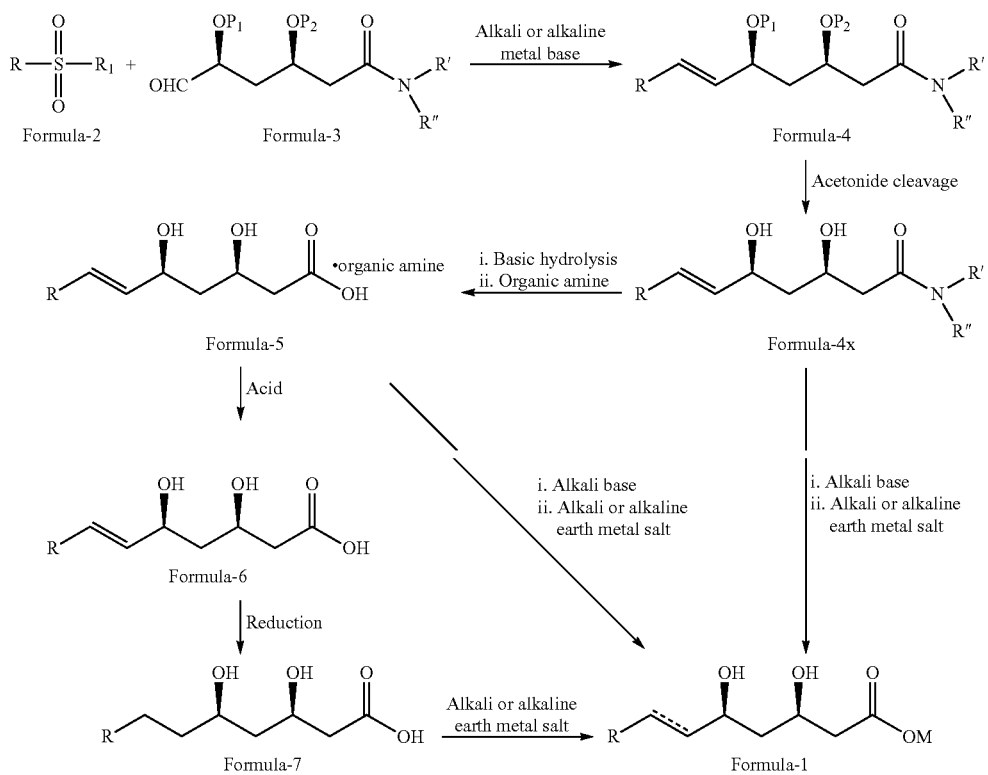

Scheme-1:

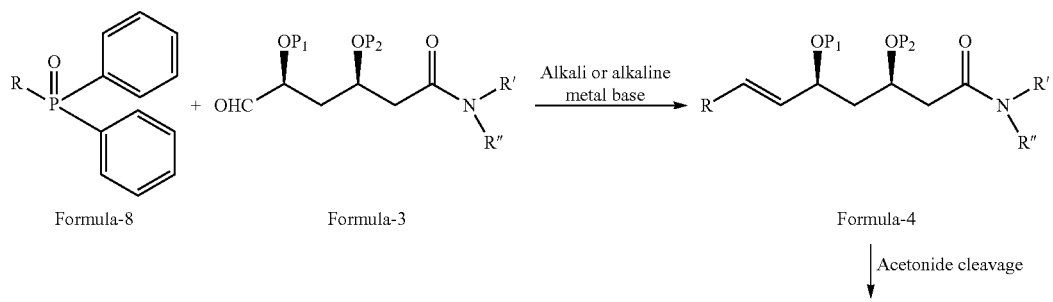

Scheme-2:

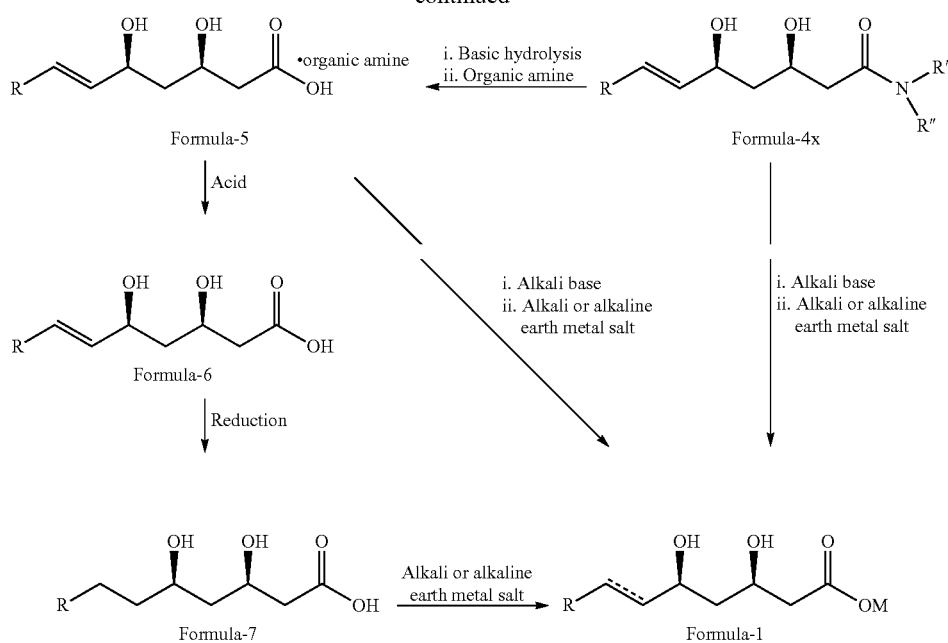
Scheme-3:
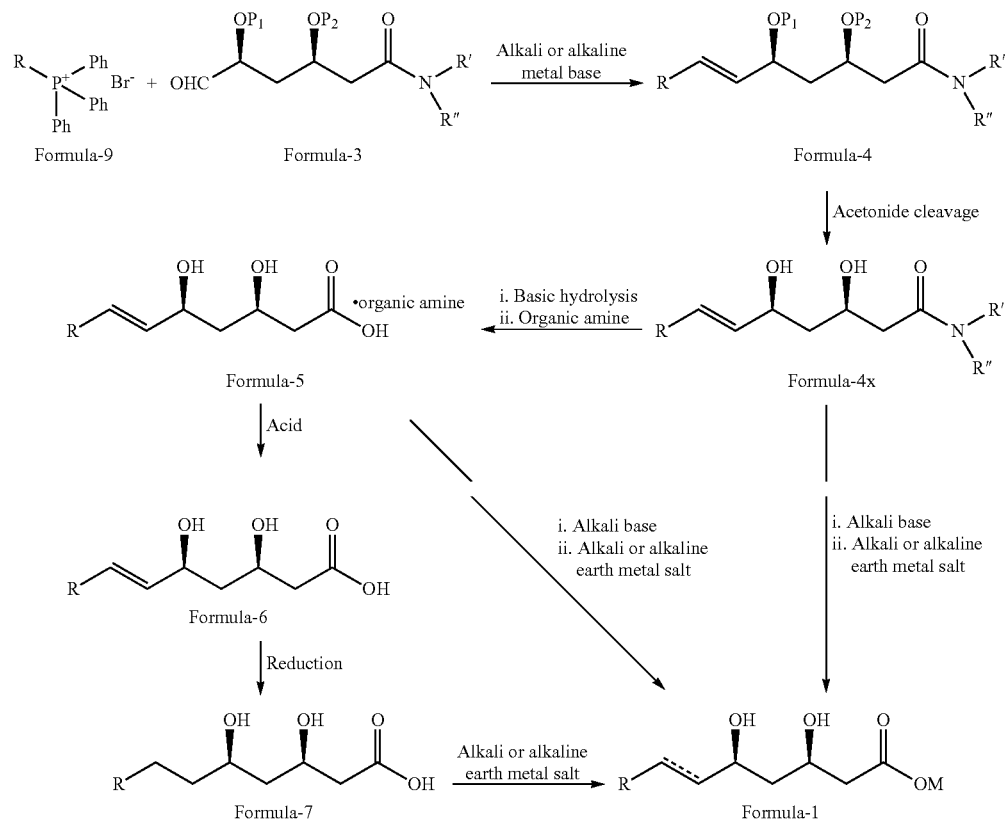

Scheme-4:
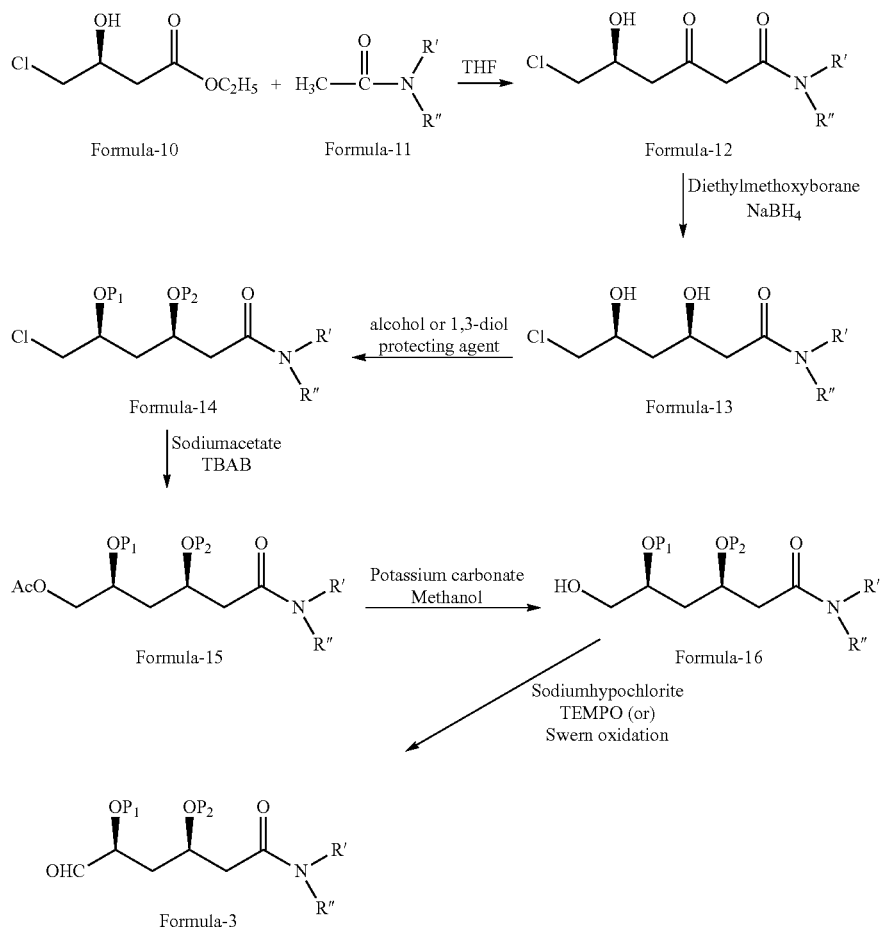
Scheme-5:
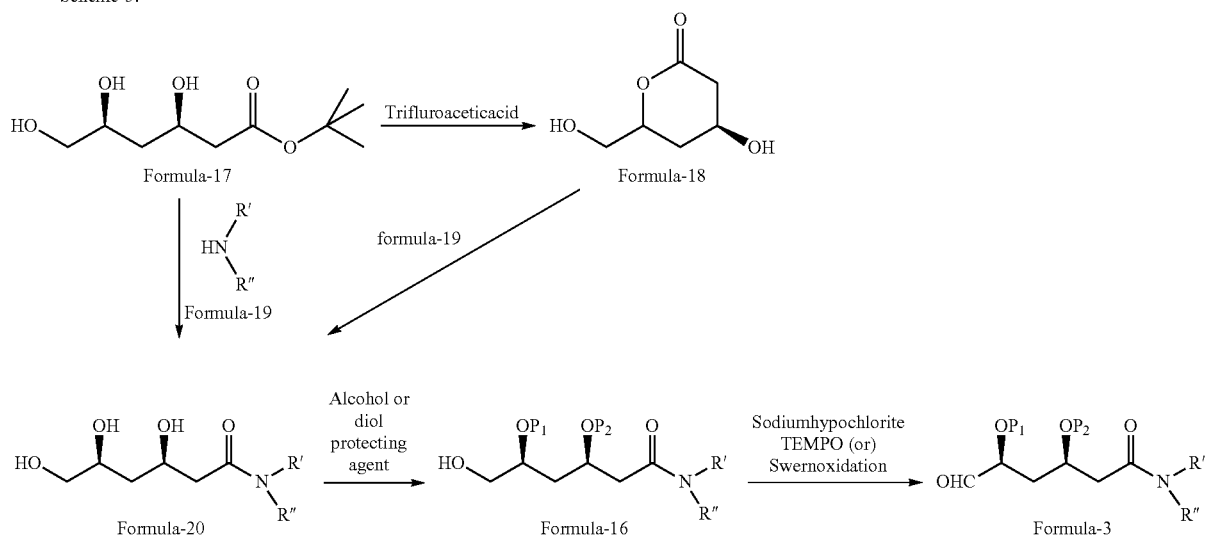

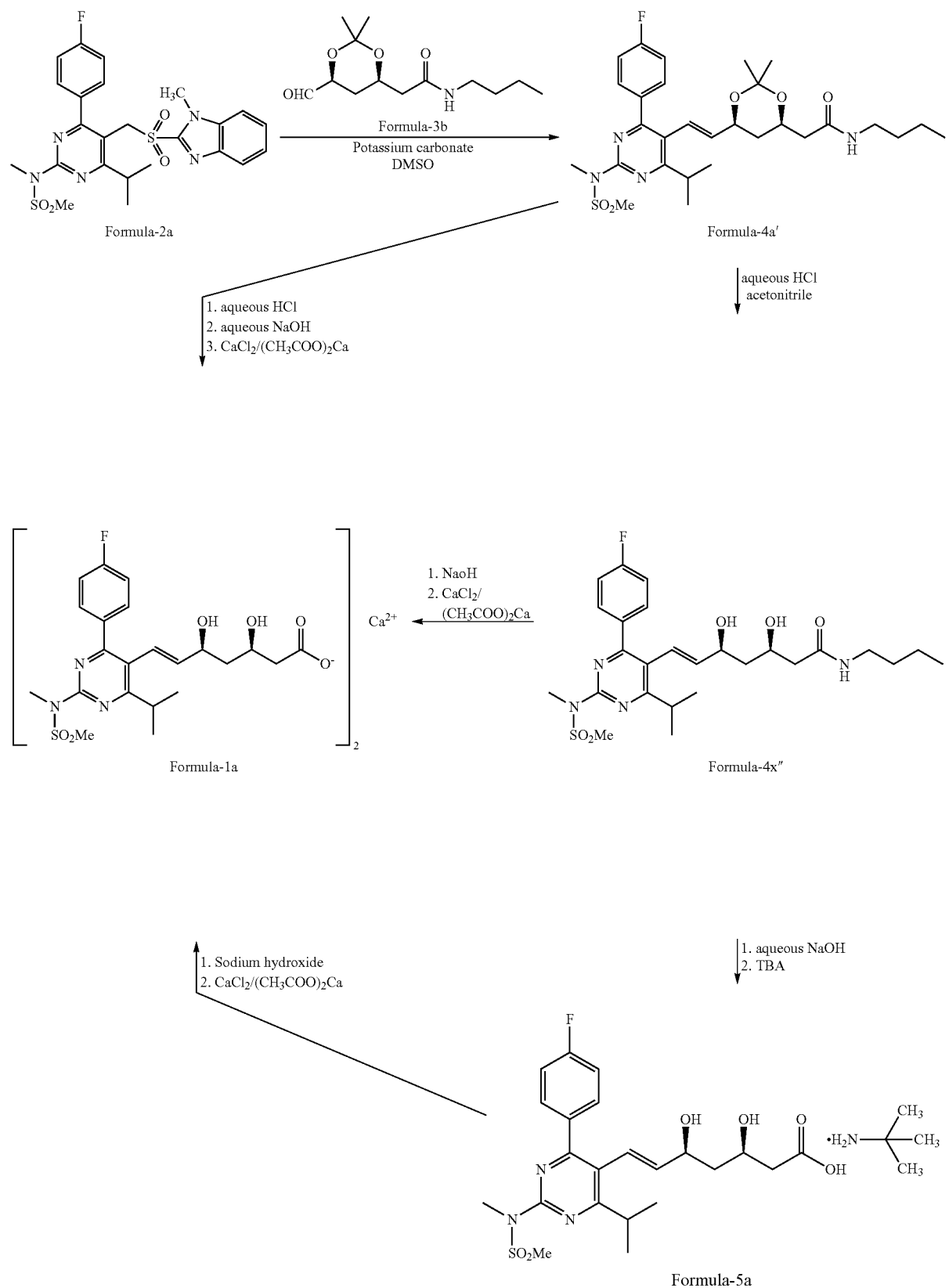

Scheme-7:
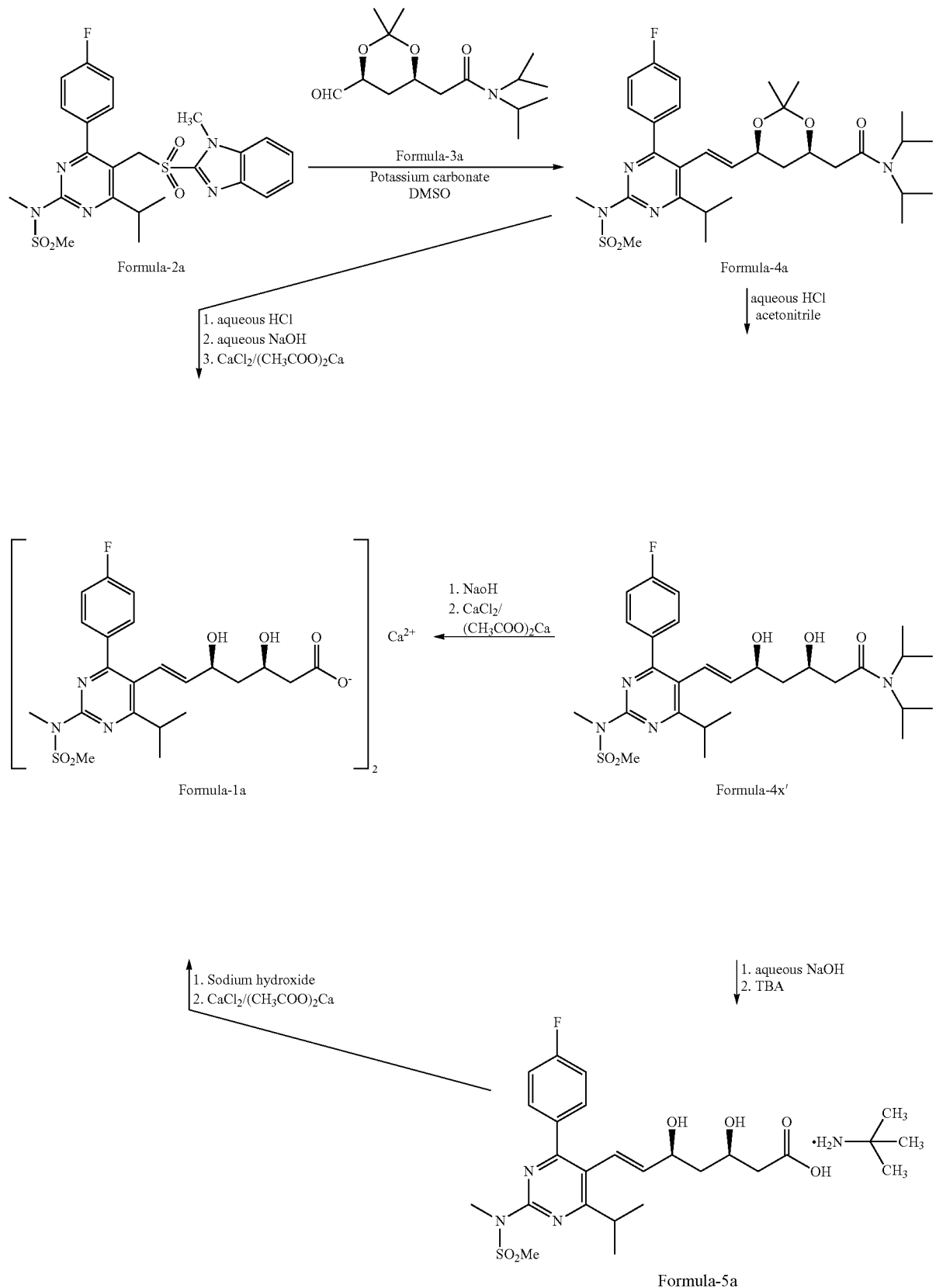

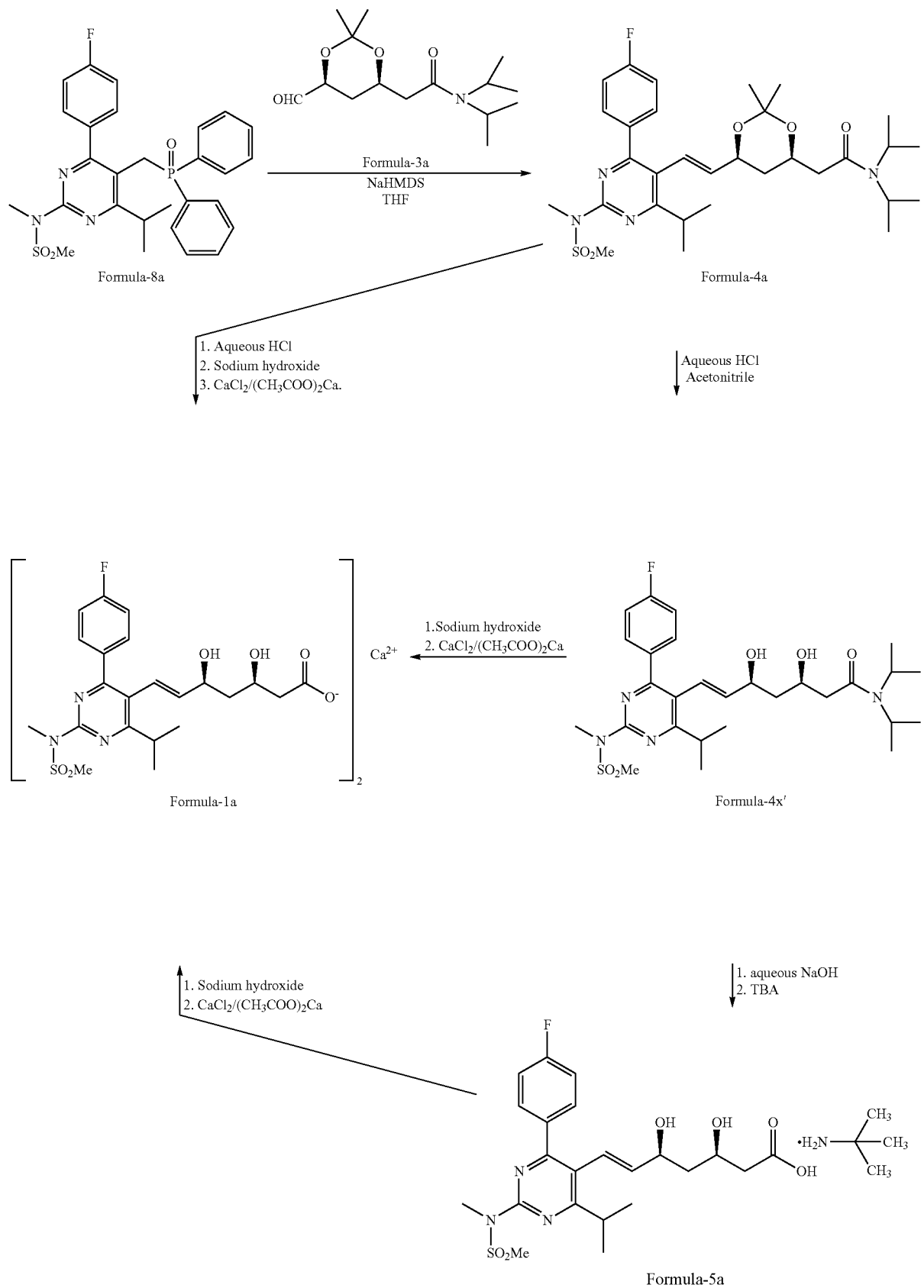

Scheme-9:
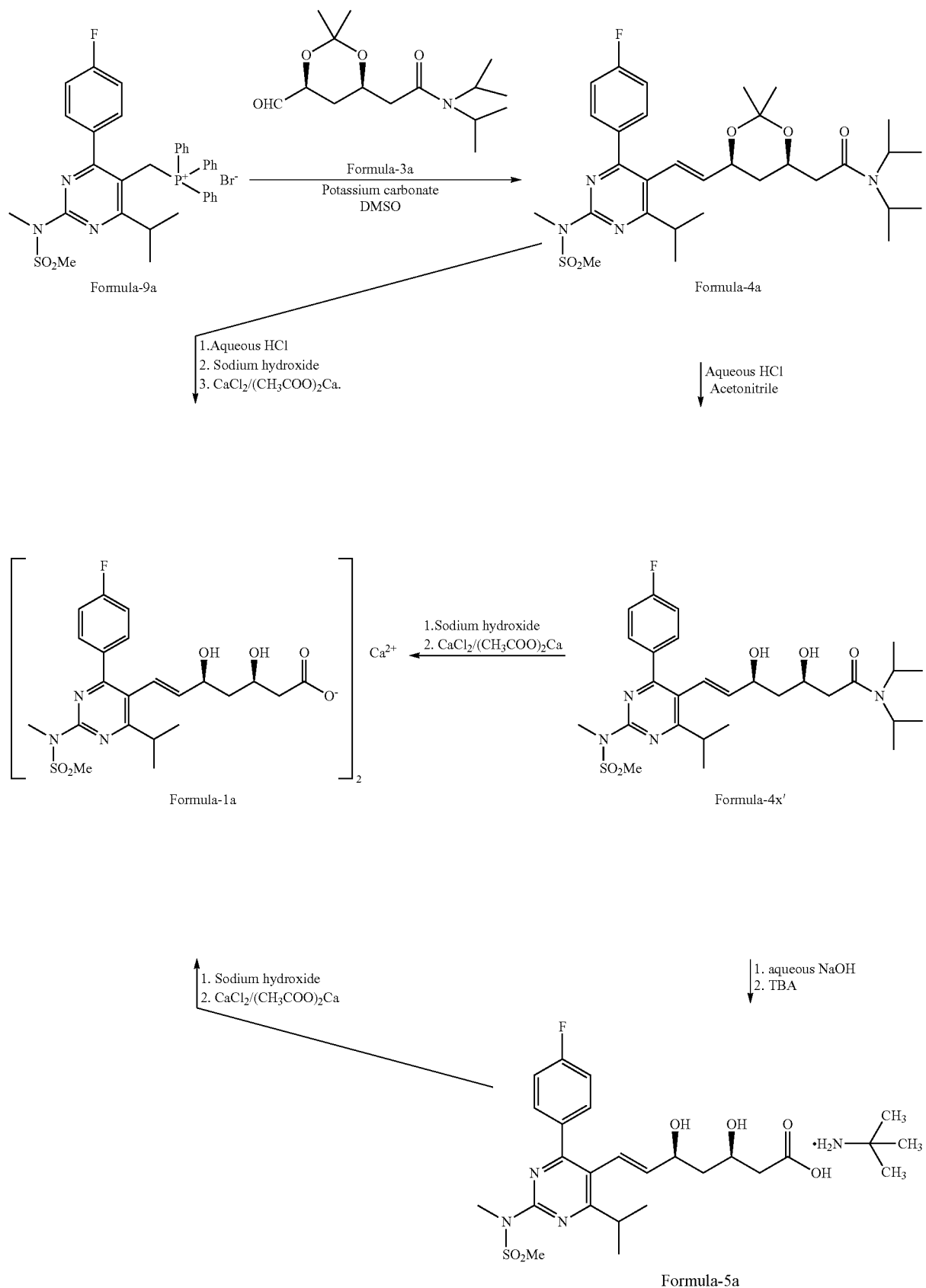

Scheme-10:
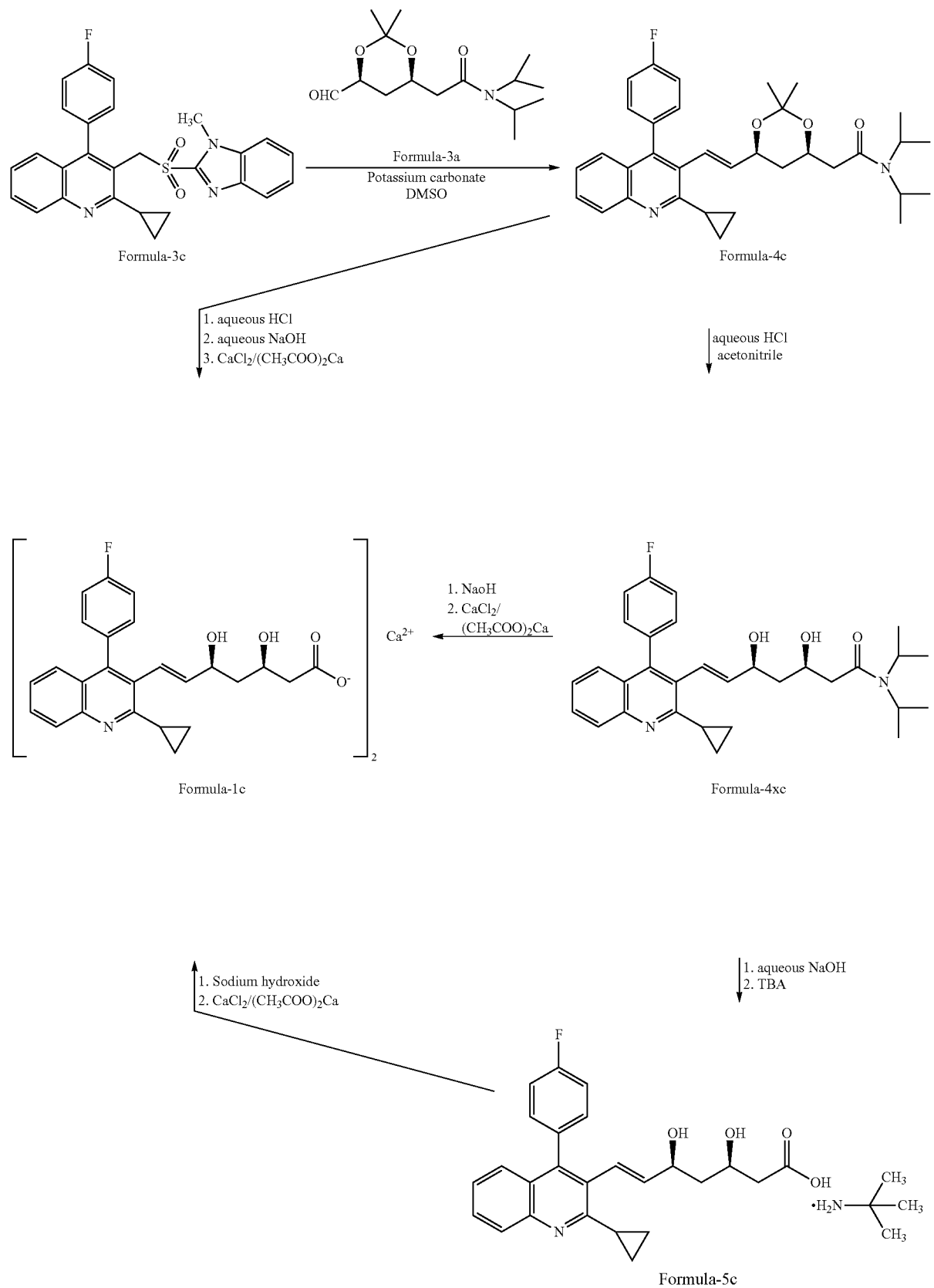

Scheme-11:
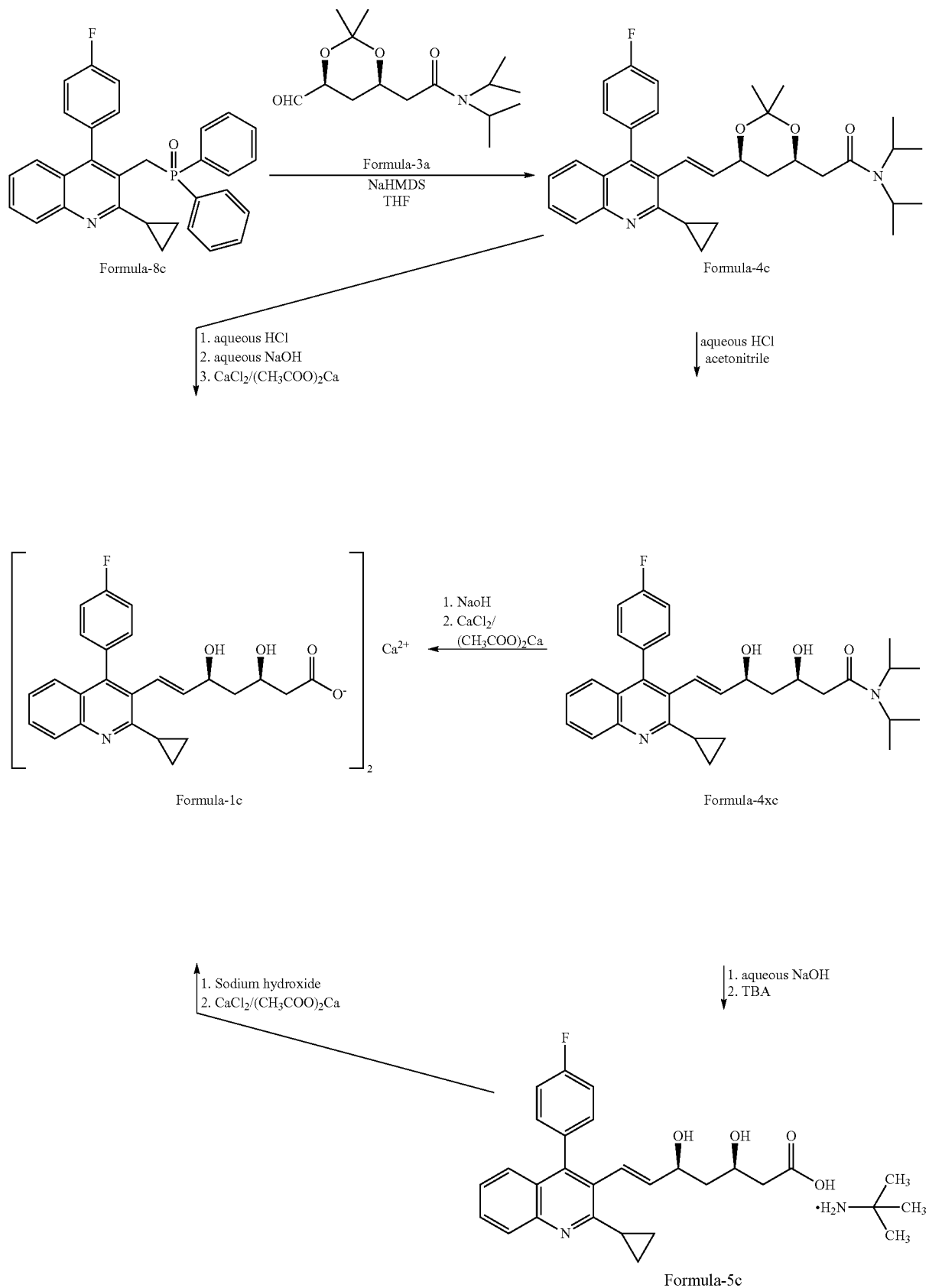

Scheme-12:
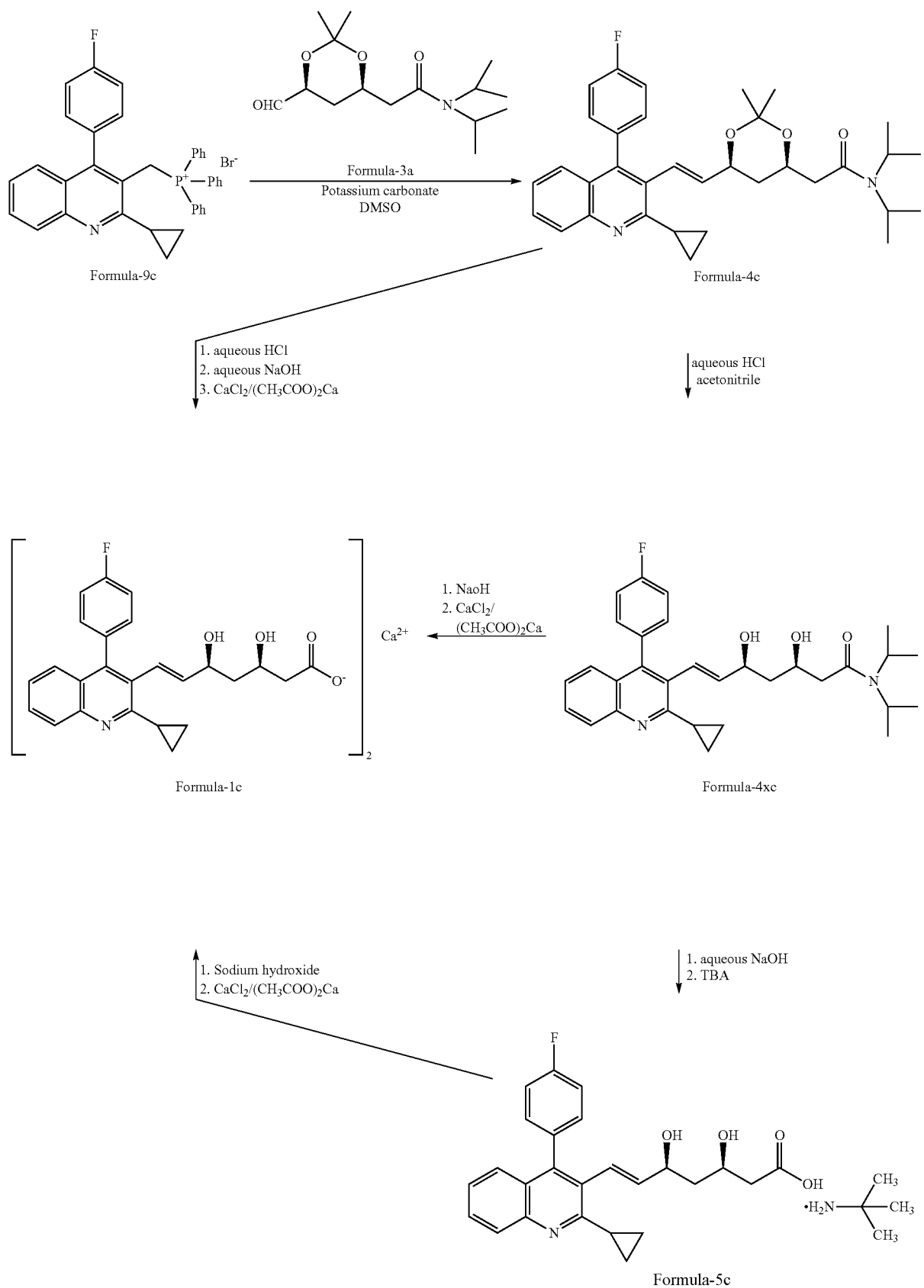

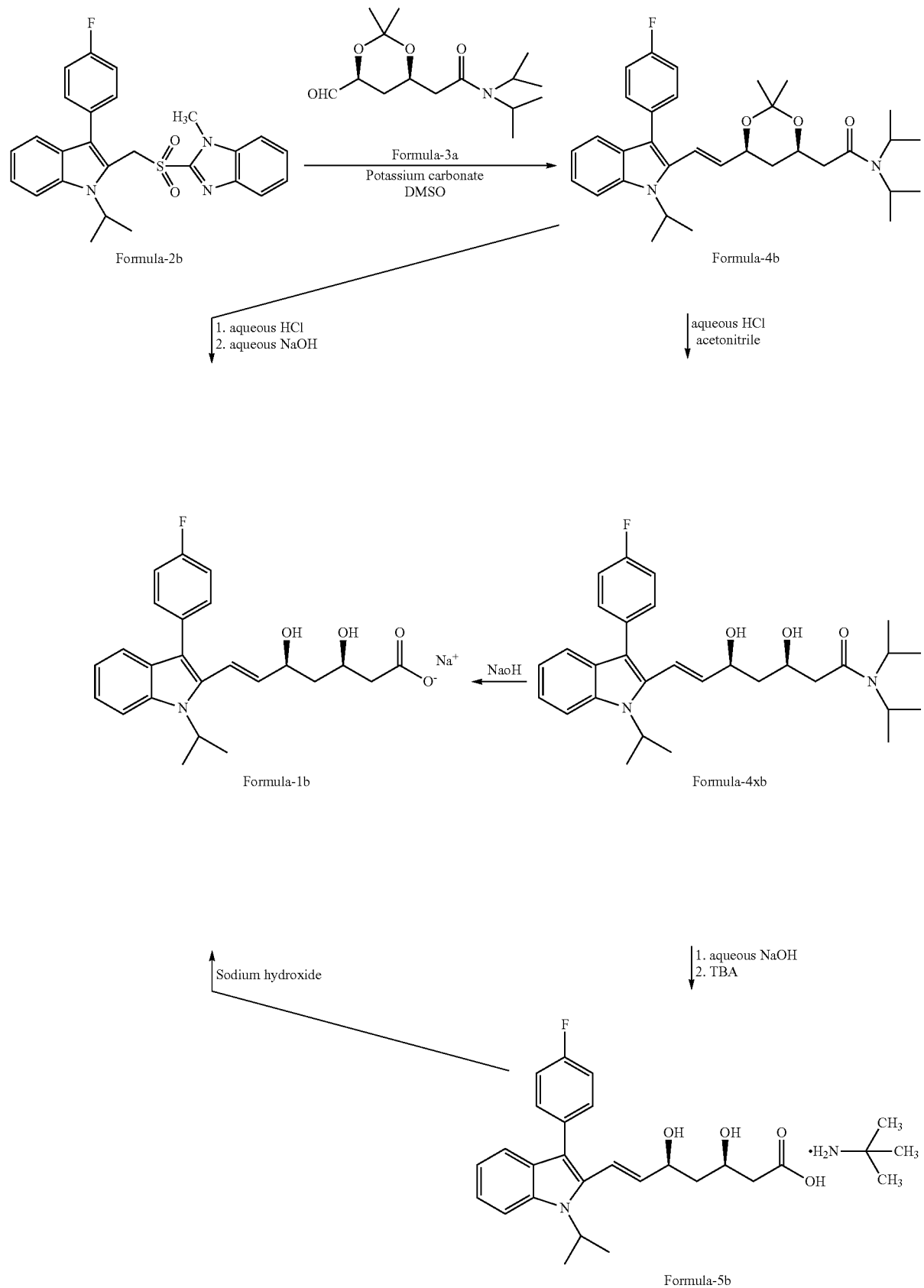

Scheme-14:
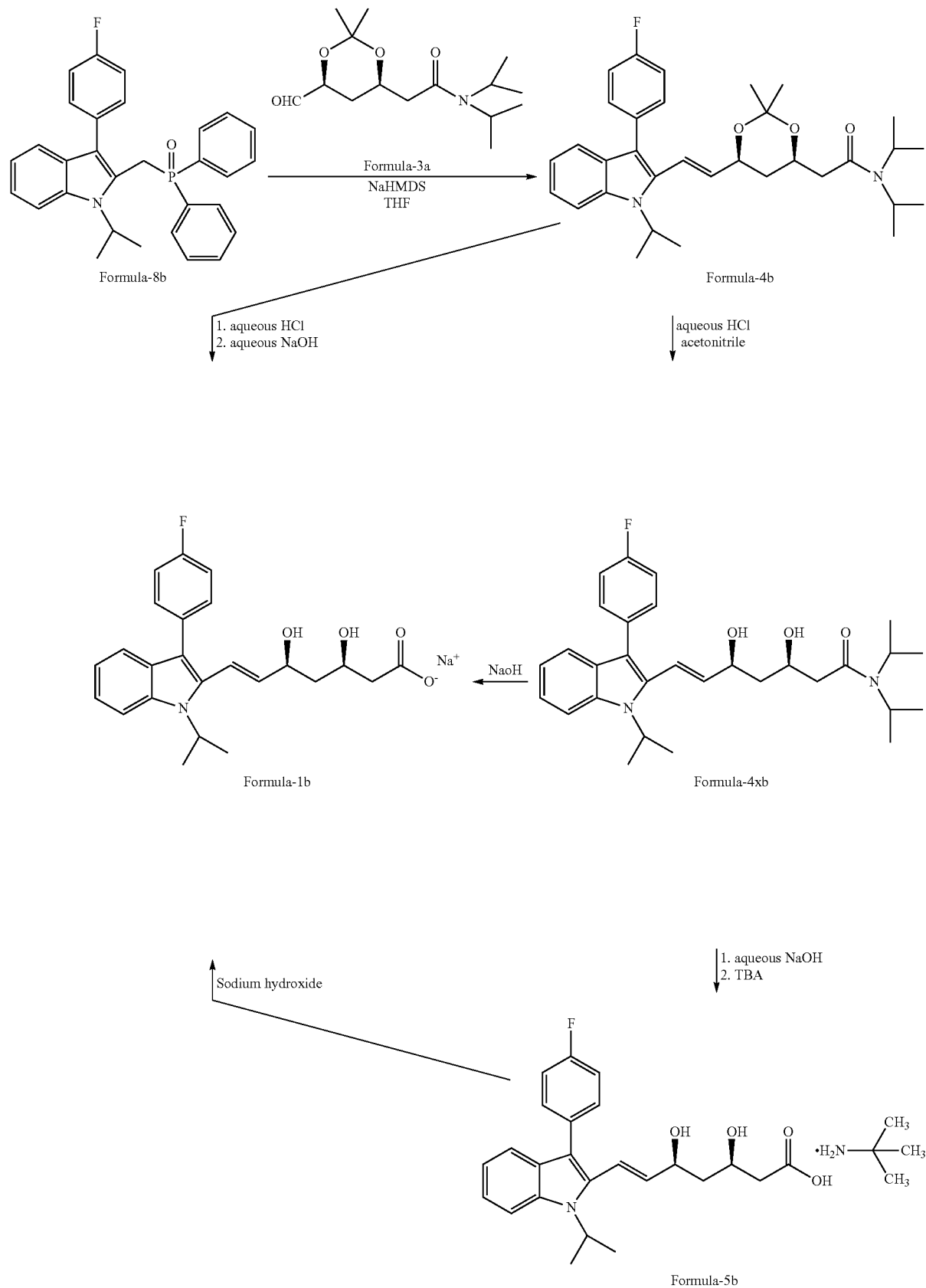

Scheme-15:

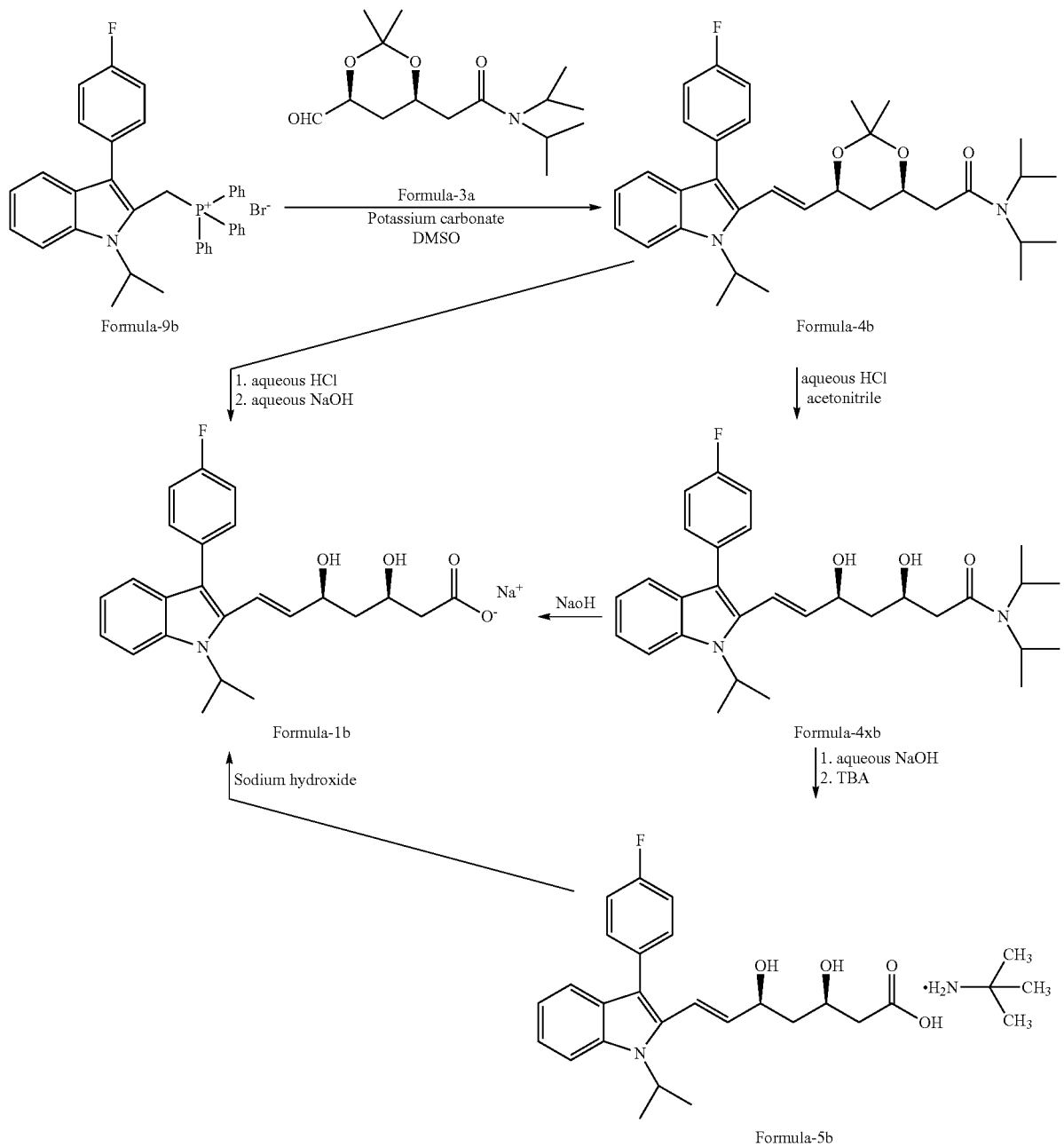

The process described in the present invention was demonstrated in examples illustrated below. These examples are provided as illustration only and therefore should not be construed as limitation of the scope of the invention.

EXAMPLES

Example-1

Preparation of Olefin Compound of Formula-4a

A mixture of compound of formula-2a (4.5 grams), dimethylsulfoxide (36 ml) and potassium carbonate (9.6 grams) was stirred for 15 minutes at 25-30° C. The reaction mixture was heated slowly to 70-75° C. A solution of n-butyl-2-((4R, 6S)-6-formyl-2,2-dimethyl-1,3-dioxan-4-yl)acetamide (3 grams) in dimethylsulfoxide (36 ml) was added to the above reaction mixture at 70-75° C. The reaction mixture was stirred at 70-75° C. for 8 hours. The reaction mixture was cooled to 25-35° C. Toluene (50 ml) was added to the reaction mixture at 25-30° C. and stirred for 45 minutes at 25-30° C. The byproduct was filtered off and washed with toluene. Water (20 ml) was added to the obtained filtrate. saturated sodium chloride solution was added to the filtrate and stirred for 10 minutes at 25-30° C. The organic and aqueous layers were separated. Extracted the aqueous layer with toluene. The total organic layer washed with water. The organic layer was purified with silica gel to remove the polar impurities. The solvent was completely distilled off under reduced pressure at below 70° C. cyclohexane (30 ml) was added to the above residue. The reaction mixture was stirred for 60 minutes at 25-30° C. Filtered the solid and washed with cyclohexane.

Yield: 3.5 grams $^1$H NMR: 0.96 (s, 3H), 1.2 (dd, 6H), 1.25 (s, 6H), 1.40 (m, 2H), 1.51 (m, 2H), 2.12 (dd, 2H), 3.00 (t, 2H), 3.43 (s, 3H), 3.5 (m, 1H), 3.53 (s, 3H), 4.20 (m, 1H), 4.50 (m, 1H), 5.51 (dd, 1H), 6.50 (d, 1H), 7.25 (m, 2H), 7.60 (m, 2H).

Mass spectrum: M$^+$ Peak at m/z–577.5

IR Spectrum: 3053, 2962, 1605, 1510, 1438, 1340, 1379, 1231, 1155, 844 and 775

M. R: 107-112° C.

Purity by HPLC: 99.93%

Example-2

Preparation of Olefin Compound of Formula-4a

Potassium carbonate (35 grams) is added to a solution of 25 grams of sulfone compound of formula-2a, 25 ml of dimethyl sulfoxide at 25 to 35° C. Added 11 grams of 2-((4R,6S)-6-formyl-2,2-dimethyl-1,3-dioxan-4-yl)-N,N-diisopropylacetamide to the above reaction mixture. Stirred the reaction mixture for 13 hours at 60 to 65° C. Quenched the reaction mixture with chilled water slowly in 30 minutes. Extracted the reaction mixture twice with ethyl acetate. Separated and washed the organic phase with saturated sodium chloride solution. Distilled the solvent completely under reduced pressure at below 70° C. Hexanes added to the residue and decanted twice then dissolved the residue in toluene and isolated the title compound using hexanes as a solvent. Dried the compound at 40-45° C. for 6 hours.

Yield: 13.5 grams.

M.R: 148-155° C.

Example-3

Preparation of Olefin Compound of Formula-4a

Diphenyl[4-(4-fluorophenyl)-6-isopropyl-2-[methyl(methyl(methylsulfonyl)amino]pyrimidin-5-yl]phosphine oxide (20 grams) compound of formula-8a dissolved in 230 ml of tetrahydrofuran by heating to 40° C. The reaction mixture was cooled to −75° C. Added sodiumbis(trimethylsilyl) amide in (100 ml of 1.0M solution in THF) to the above reaction mixture. Stirred the reaction for 1 hour at −75° C. Added a solution of 2-((4R,6S)-6-formyl-2,2-dimethyl-1,3-dioxan-4-yl)-N,N-diisopropylacetamide (30 grams in 100 ml toluene) to the above reaction mixture at below −75° C. The reaction mixture allowed to raise the temperature of 10° C. Added 3.21 gram of glacial acetic acid and 15 gram of water to the above reaction mixture. Distilled off the solvent to get the concentrated reaction mixture under reduced pressure at 94° C. The reaction mixture was cooled to 20° C. Quenched the reaction mixture with water followed by sodium hydrogen carbonate solution. Separated the organic and aqueous phases. Distilled off the solvent completely under reduced pressure at 116° C. The residue treated with methanol and allowed to cool to 20° C. The precipitated solid cooled to 2° C. Stirred the reaction mixture for 30 minutes. The solid obtained is filtered and dried to get the title compound Yield: 12 grams Example-4

Preparation of Olefin Compound of Formula-4a

Added a solution of 2-((4R,6S)-6-formyl-2,2-dimethyl-1,3-dioxan-4-yl)-N,N-diisopropylacetamide of formula-3a in 80 grams of dimethylsulfoxide to a mixture of 260 grams of triphenyl[4-(4-fluorophenyl)-6-isopropyl-2-[methyl(methyl (methylsulfonyl)amino]pyrimidin-5-ylmethyl]phosphonium bromide compound of formula-9a and 80 grams of potassium carbonate. Heated the reaction mixture to 70-75° C. Stirred the reaction mixture for 3.5 hours. Cooled the reaction mixture to 25-30° C. Added 1500 ml of toluene to the above reaction mixture. Stirred the reaction mixture for 30 minutes at 25-35° C. Filter the reaction mixture and washed with toluene. Washed the organic layer with water. Distilled off the solvent completely under reduced pressure at below 70° C. Cooled the reaction mixture to 40° C. Treated the reaction mixture with methanol. Added 750 ml of petroleum ether to the above reaction mixture. Heated the reaction mixture to reflux. Stirred at reflux for 30 minutes. Cooled the reaction mixture to 25-35° C. Stirred the reaction mixture for 1 hour at 25-35° C. Cooled the reaction mixture to 0-10° C. Stirred for 1 hour at 0-10° C. Filtered the precipitated solid. Dried the obtained solid at 50-60° C. to get the title compound.

Yield: 110 grams.

Example-5

Preparation of Olefin Compound of Formula-4a'

Following the procedure similar to that described in example-4, n-butyl-2-((4R,6S)-6-formyl-2,2-dimethyl-1,3-dioxan-4-yl)acetamide used in place of 2-((4R,6S)-6-formyl-2,2-dimethyl-1,3-dioxan-4-yl)-N,N-diisopropylacetamide gives the title compound.

Example-6

Preparation of Dihyroxycompound of Formula-4-x"

The compound of formula-4a (10 grams) was dissolved in 100 ml of acetonitrile at 25-30° C. The reaction mixture was cooled to 23-28° C. Aqueous hydrochloric acid (0.30 ml in 28 ml of water) was added to the reaction mixture slowly at 23-28° C. Stirred the reaction mixture for 4 hours at 23-28° C. The reaction mixture was quenched with aqueous sodium bicarbonate solution at 23-28° C. Sodium chloride solution was added to the reaction mixture and stirred for 15 minutes. Organic and aqueous layers were separated. The solvent from organic layer was completely distilled off under reduced pressure at below 50° C. Cyclohexane (60 ml) was added to the above obtained residue. The reaction mixture was stirred for 60 minutes at 25-30° C. Filtered the solid obtained and washed with cyclohexane.

Yield: 6.5 grams.

$^1$H NMR: 1.20 (dd, 6H), 1.51 (m, 2H), 2.12 (dd, 2H), 3.40 (m, 1H), 3.43 (s, 3H), 3.53 (s, 3H), 4.00 (m, 1H), 5.51 (dd, 1H), 6.50 (d, 1H), 7.26 (t, 2H), 7.70 (dd, 2H)

Mass spectrum: M$^+$ peak at m/z–559.6

IR spectrum: 3380, 2967, 1601, 1547, 1509, 1437, 1334, 1382, 1228, 1153, 843, 775 cm$^{-1}$.

M.R: 92-100° C.

Purity by HPLC: 98.45%.

Example-7

Preparation of Tertiary Butylamine Compound of Formula-5a

The dihydroxy compound of formula-4-x" (5 grams) was dissolved in 25 ml of ethylene glycol at 25-30° C. Aqueous sodium hydroxide solution (2.5 grams in 10 ml of water) was added to the above reaction mixture. The reaction mixture was heated to 90-95° C. Stirred the reaction mixture for 4 hours at 90-95° C. Cooled the reaction mixture to 25-30° C. Water (50 ml) was added to the reaction mixture at 25-30° C. The reaction mixture was quenched with aqueous hydrochloric acid. Ethylaceate (100 ml) was added to the reaction mixture. The organic and aqueous layers were separated. The ethyl acetate layer was cooled to 0-10° C. Tertiary butylamine (5 ml) was added to the above reaction mixture at 0-10° C. The reaction mixture was stirred for 45 minutes at 0-10° C. The solvent was completely distilled off under reduced pressure at below 50° C. Acetonitrile (15 ml) was added to the above residue and distilled off completely under reduced pressure at below 50° C. Acetonitrile (25 ml) was added to the above reaction mixture and stirred for 1.5 hours at 25-30° C. Cooled the reaction mixture to 0-10° C. and stirred for 60 minutes. The solid obtained was filtered off and washed with acetonitrile. The obtained solid was dried at 50-55° C. to get the title compound.

Yield: 3 grams
M.R: 163-167° C.
Purity by HPLC: 99.58%

Example-8

Preparation of Tertiary Butylamine Compound of Formula-5a

The dihydroxy compound of formula-4-x" (5 grams) was dissolved in 25 ml of isopropyl alcohol at 25-30° C. Aqueous sodium hydroxide solution (2.5 grams in 10 ml of water) was added to the above reaction mixture. The reaction mixture was heated to reflux. Stirred the reaction mixture for 4 hours at reflux. Cooled the reaction mixture to 25-30° C. Water (50 ml) was added to the reaction mixture at 25-30° C. The reaction mixture was quenched with aqueous hydrochloric acid. Ethylaceate (100 ml) was added to the reaction mixture. The organic and aqueous layers were separated. The ethyl acetate layer was cooled to 0-10° C. Tertiary butylamine (5 ml) was added to the above reaction mixture at 0-10° C. The reaction mixture was stirred for 45 minutes at 0-10° C. The solvent was completely distilled off under reduced pressure at below 50° C. Acetonitrile (15 ml) was added to the above residue and distilled off the acetonitrile completely under reduced pressure at below 50° C. Acetonitrile (25 ml) was added to the above reaction mixture and stirred for 1.5 hours at 25-30° C. Cooled the reaction mixture to 0-10° C. and stirred for 60 minutes. The solid obtained was filtered off and washed with acetonitrile. The obtained solid was dried at 50-55° C. to get the title compound.

Yield: 3.2 grams
M.R: 163-167° C.
Purity by HPLC: 99.53%

Example-9

Preparation of Tertiary Butylamine Compound of Formula-5a

A solution of 25 grams of olefin compound of formula-4a and 250 ml of acetonitrile, is cooled to 23 to 28° C. Added 70.75 ml of 1.0% hydrochloric acid solution slowly to the above contents of the reaction. Stirred the reaction mixture for 4 hours at 23 to 28° C. Added 37.5 ml of 10% sodium hydroxide solution to the reaction mixture and stirred to 2 hours at 35-40° C. Adjust the pH of the reaction mixture to 3.5 to 4.5 with 10% hydrochloride. Separated the organic phase and cooled to 0-10° C. Added 8.66 grams of tertiary butylamine to the contents and stirred for 1 hour at 0-5° C. Distilled the solvent completely and isolated the title compound using acetonitrile as a solvent. Dried the compound to get the title compound.

Yield: 18 grams.

Example-10

Preparation of Compound of Formula-17

The tert-butyl 2-((4R,6S)-6-(hydroxymethyl)-2,2,-dimethyl-1,3-dioxan-4-yl)acetate (50 grams) was dissolved in 500 ml of acetonitrile. The reaction mixture was cooled to 25-30° C. Aqueous hydrochloric acid solution (7.5 ml of hydrochloric acid in 125 ml of water) was added to the above reaction mixture slowly at 25-30° C. for 2 hours. The reaction mixture was stirred for 2 hours at 25-30° C. The reaction mixture was quenched with aqueous sodium bicarbonate solution. The reaction mixture was stirred for 30 minutes. The organic and aqueous layers were separated. The aqueous layer was extracted with ethyl acetate. The organic layer was combined and dried over sodium sulfate. The solvent was completely distilled off under reduced pressure at below 50° C. to get the title compound as a residue.

Yield: 40 grams
$^1$H NMR: 1.4 (s, 9H), 1.50 (m, 2H), 2.5 (d, 2H), 3.2 (m, 1H), 3.6-3.9 (m, 2H), 3.95 (m, 1H)
Mass spectrum: M$^+$ peak at m/z–243.3
IR Spectrum: 3433, 1715 cm$^{-1}$.

Example-11

Preparation of Dihydroxy Amide Compound of Formula-20b

A mixture of (3R,5S)-tert-butyl 3,5,6-trihydroxyhexanoate compound of formula-17 (8 grams) and n-butyl amine 19 b (40 grams) was stirred for 10 minutes. The reaction mixture was heated to reflux temperature of 78-82° C. The reaction mixture was stirred for 15 hours at reflux temperature. The n-butylamine was completely distilled off from the reaction mixture at below 60° C. The obtained residue was purified using silica gel with a mixture of ethyl acetate and cyclohexane as a solvent system to get the title compound as a residue.

Yield: 7.5 grams
$^1$H NMR: 0.9 (t, 3H), 1.3 (m, 2H), 1.5 (m, 4H), 2.2 (t, 2H), 3.0 (m, 3H), 3.25 (m, 1H), 4.75 (m, 2H).
Mass spectrum: M$^+$ Peak at m/z–242.5
IR Spectrum: 3485 and 1634 cm$^{-1}$.

Example-12

Preparation of Protected Dihyroxy Compound of Formula-16b

A mixture of (3R,5S)—N-butyl-3,5,6-trihydroxy hexanamide compound of formula-20b (23 grams) and 290 ml of acetone was stirred for 10 minutes at 25-30° C. The reaction mixture was cooled to 10-15° C. Dimethoxypropane (290 ml)

and methane sulfonic acid (0.5 ml) was added to the above reaction mixture at 10-15° C. Stirred the reaction mixture for 4 hours at 10-15° C. Quenched the reaction mixture with aqueous sodium bicarbonate solution. cyclohexane (120 ml) was added and stirred for 30 minutes at 25-30° C. The organic and aqueous layers were separated. The aqueous layer was extracted with cyclohexane. The solvent was completely distilled off from the reaction mixture. The obtained crude compound was purified by column chromatography using a mixture of cyclohexane and ethyl acetate to get the title compound as a semi-solid.

Yield: 18 grams $^1$H NMR: 0.9 (t, 3H), 1.3 (m, 2H), 1.40 (s, 6H), 1.5 (m, 2H), 1.75 (m, 2H), 2.4 (d, 2H), 3.6 (t, 2H), 4.10 (m, 2H), 4.15 (m, 1H), 4.2 (m, 1H).

Mass spectrum: M$^+$ peak at m/z–282.2

IR spectrum: 3068, 3480, 1634 cm$^{-1}$.

Example-13

Preparation of Amide Compound of Formula-3b

A mixture of methylene chloride (6 ml) and oxalyl chloride (1.46 grams) was cooled to −75 to −65° C. under nitrogen atmosphere. A mixture of methylene chloride (6 ml) and dimethyl sulfoxide (1.36 ml) was added to the above reaction mixture at −75 to −65° C. in 45 minutes. Stirred the reaction mixture for 45 minutes at −65 to −60° C. A solution of N-butyl-2-((4R,6S)-6-(hydroxymethyl)-2,2-dimethyl-1,3-dioxan-4-yl)acetamide (2 grams) in methylene chloride (10 ml) was added slowly to the above reaction mixture in 60 minutes at −65 to −60° C. Stirred the reaction mixture for 45 minutes at −65 to −60° C. Triethylamine (5 ml) was slowly added at −65 to −60° C. to the above reaction mixture. Stirred the reaction mixture for 60 minutes at −65 to −60° C. The reaction mixture was added to the 40 ml of ice water. The pH of the reaction mixture was adjusted to 7 with aqueous acetic acid solution. Stirred the reaction mixture for 10 minutes. The organic and aqueous layers were separated. The aqueous layer was extracted with methylene chloride. The organic layer was washed with water followed by with saturated sodium chloride solution. The organic layer was dried over sodium sulfate. The solvent from the organic layer was completely distilled off and finally expelled with nitrogen.

Yield: 1.8 grams $^1$H NMR: 0.9 (t, 3H), 1.3 (m, 2H), 1.40 (s, 6H), 1.45 (m, 2H), 1.5 (m, 2H), 2.5 (d, 2H), 3.2 (d, 2H), 4.0 (m, 2H), 9.5 (s, 1H).

Mass spectrum: M$^+$ peak at m/z–258.3

IR Spectrum: 3093, 1720, 1634 cm$^{-1}$.

Example-14

Preparation of (S) 6-chloro-5-hydroxy-N,N-diisopropyl-3-oxo hexanamide (Formula-12a)

N—N-diisopropylacetamide (70 grams) added to a solution of 3500 ml of 1 molar LiHMDS solution, 650 ml of tetrahydrofuran at −50 to −70° C. Stirred the reaction mixture for 25 minutes at −70 to −75° C. Added 185 gram of ethyl-4-chloro-3-hydroxy butanoate at −73 to −75° C. Stirred the reaction for 1 hour at −48 to −45° C. Quenched the reaction mixture with chilled water followed by hydrochloric acid solution. Separated the organic and inorganic phases. Washed the organic layer with 10% sodium bicarbonate solution. Dried the organic layer using sodium sulfate and distilled the solvent completely under reduced pressure. Purified the residue in petroleum ether to get the title compound of formula-12.

Yield: 240 grams

Example-15

Preparation of (3R,5S)-6-chloro-3,5-dihydroxy-N,N-diisopropylhexanamide (Formula-13a)

Added 430 ml of diethyl methoxy borane to a cooled solution of 500 grams of (S) 6-chloro-5-hydroxy-N,N-diisopropyl-3-oxohexanamide, 3500 ml tetrahydrofuran and 1000 ml of methanol at −75 to −70° C. Stirred the reaction mixture at −75 to −70° C. for 25 minutes. Added 86.5 grains of sodium borohydride in lot wise. Stirred the reaction mixture for 2 hours at −75 to −70° C. Quenched the reaction mixture with hydrogen peroxide solution. Separated the organic and inorganic phases. Washed the organic layer with 10% sodium bicarbonate solution followed brine solution and water. Dried the organic layer over sodium sulphate. Distilled the solvent completely under reduced pressure to get the title compound as a residue.

Yield: 446 grams

Example-16

Preparation of 2-((4R,6S)-6-(chloromethyl)-2,2-dimethyl-1,3-dioxan-4-yl)-N,N-diisopropylacetamide (Formula-14a)

2,2-dimethoxy propane (1050 ml) and 2.6 ml of methane sulfonic acid added to a solution of 280 grams of (3R,5S)-6-chloro-3,5-dihydroxy-N,N-diisopropylhexanamide, 1500 ml of acetone. Stirred the reaction mixture for 3 hours at 25-35° C. Quenched the reaction mixture with sodium bicarbonate solution. Separated the organic and inorganic phases. Extracted the aqueous layer with petroleum ether and washed the organic layer with brine solution. Dried the organic layer over sodium sulfate. Distilled the solvent completely under reduced pressure to get the title compound as a residue.

Yield: 254 grams

Example-17

Preparation of ((4S,6R)-6-(((diisopropylcarbamoyl)methyl)-2,2-dimethyl-1,3-dioxan-4-yl)methyl acetate (Formula-15a)

Heated the reaction mixture of 250 grams of 2-((4R,6S)-6-(chloromethyl)-2,2-dimethyl-1,3-dioxan-4-yl)-N,N-diisopropylacetamide, 225 grams of sodium acetate and 290 grams of tetra butyl ammonium bromide to 110-115° C. Stirred the reaction for 12 hours at 110-115° C. Diluted the reaction mixture with petroleum ether and filtered the byproduct. Organic layer washed with water. Distilled the solvent completely under reduced pressure. Isolated the material in petroleum ether. Dried the material at 40-45° C. to get the title compound.

Yield: 100 grams

Example-18

Preparation of 2-((4R,6S)-6-(hydroxymethyl)-2,2-dimethyl-1,3-dioxan-4-yl)-N,N-diisopropylacetamide (Formula-16a)

Potassium carbonate (150 grams) added to a solution of 50 grams of ((4S,6R)-6-(((diisopropylcarbamoyl)methyl)-2,2- dimethyl-1,3-dioxan-4-yl)methyl acetate in 250 ml methanol. Stirred the reaction mixture at 0-5° C. for 2 hours. Quenched the reaction mixture with chilled water. Stirred the reaction mixture for 20 minutes. Extracted the reaction mixture thrice with dichloromethane. Washed the organic layer with brine and water. Dried the organic layer over sodium sulfate and distilled the solvent completely under reduced pressure to get the title compound.

Yield: 35 grams

Example-19

Preparation 2-((4R,6S)-6-formyl-2,2-dimethyl-1,3-dioxan-4-yl)-N,N-diisopropyl acetamide (Formula-3a)

1 gram of potassium bromide and 0.1 gram of 2,2,6,6-tetramethyl-1-piperidinyloxy free radical is added to the a solution of 25 grams of 2-((4R,6S)-6-(hydroxymethyl)-2,2-dimethyl-1,3-dioxan-4-yl)-N,N-diisopropylacetamide in methylene chloride at 0-5° C. Added sodium hypochlorite to the above reaction mixture at 0-5° C. in 1 hour. Stirred the reaction for 30 minutes at 0-5° C. Quenched the reaction mixture with 10% sodium thio sulphate solution. Separated the organic and inorganic phases. Washed the organic layer with water. Dried the organic layer over sodium sulfate. Distilled the solvent completely under reduced pressure to get the title compound.

Yield: 10 grams

Example-20

Preparation of Compound of Formula-1a

The dihydroxy compound of formula-4x (1 gram) was dissolved in 5 ml of ethylene glycol at 25-30° C. Aqueous sodium hydroxide solution (05 gram in 2 ml) was added to the above reaction mixture at 25-30° C. The reaction mixture was heated to 90-95° C. The reaction mixture was stirred at 90-95° C. for 4 hours. The reaction mixture was cooled to 25-30° C. Water (5 ml) was added to the above reaction mixture at 25-30° C. Quenched the reaction mixture with aqueous hydrochloric acid. Ethyl acetate (20 ml) was added to the reaction mixture and stirred for 10 minutes at 25-30° C. The ethyl acetate layer was separated. The pH of the reaction mixture was adjusted to 9.2 with aqueous sodium hydroxide solution. The solvent completely distilled off under reduced pressure at below 50° C. The reaction mixture was filtered through hyflow and washed with water. Calcium chloride solution was added to the reaction mixture was slowly at 25-35° C. Stirred the reaction mixture was 60 minutes at 35-45° C. The solid was filtered and washed with water.

Yield: 0.7 grams:

$^1$H NMR: 1.20 (dd, 6H), 1.32 (m, Hb), 1.51 (m, Ha), 1.98 (dd, Hb), 2.12 (dd, Ha), 3.38 (m, 1H), 3.43 (s, 3H), 3.53 (s, 3H), 3.76 (m, 1H), 4.19 (q, 1H), 5.51 (dd, 1H), 6.50 (d, 1H), 7.26 (t, 2H), 7.70 (dd, 2H).

Mass spectrum: M$^+$ peak at m/z−481

IR spectrum: 3380, 2967, 1601, 1547, 1509, 1437, 1334, 1382, 1228, 1153, 843, 775 cm$^{-1}$.

Purity by HPLC: 99.50%

Example-21

Preparation of Calcium Salt Compound of Formula-1a

A solution of 15 grams of tertiary butylamine salt compound of formula-5a and 75 ml of water is cooled to 25-30° C. Added 8.5 ml of 10% sodium hydroxide solution. Stirred for 1 hour. Adjusted the pH of the reaction mixture to 9.1 by extracting the reaction mixture thrice with tertiary butyl acetate. Added the aqueous phase of the reaction mixture to a solution of 2.55 grams of calcium chloride and 15 ml of water at 35 to 45° C. Filtered off the precipitated compound. Dried the compound at 40-45° C.

Yield: 12 grams

Particle Size: D (v, 0.1) is 4.9 μm; D (v, 0.5) is 45.86 μm; D (v, 0.9) is 180.59 μm.

Particle Size after micronization: D (v, 0.1) is 2.46 μm; D (v, 0.5) is 12.85 μm; D (v, 0.9) is 46.43 μm.

Example-22

Preparation of Calcium Salt Compound of Formula-1a

A solution of 15 grams of tertiary butylamine salt compound of formula-5a and 75 ml of water is cooled to 25-30° C. Added 8.5 ml of 10% sodium hydroxide solution. Stirred for 1 hour. Adjusted the pH of the reaction mixture to 9.1 by extracting the reaction mixture thrice with tertiary butyl acetate. Added calcium chloride solution (2.55 grams in 15 ml of water) to the aqueous phase of the reaction mixture at 35 to 45° C. Filtered off the precipitated compound. Dried the compound at 40-45° C.

Yield: 11.5 grams

Bulk density: 0.83 g/ml; Tapped density: 0.91 g/ml

Bulk density after micronisation: 0.36 g/ml;

Tapped density after micronisation: 0.59 g/ml

We claim:

1. A process for the preparation of a compound of Formula-4,

Formula-4 wherein denotes a single or a double bond and R is represented by Formula-a,

Formula-a wherein:

$P_1$ and $P_2$ are alcohol protecting groups or $P_1$ and $P_2$, taken together, form a 1,3-diol protecting group, R' is hydrogen and R" is n-butyl, the process comprising:
reacting a compound of Formula-2,

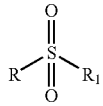

Formula-2 wherein R is defined as above and is linked to the sulphur atom with a methylene group (—CH$_2$—) and R$_1$ is

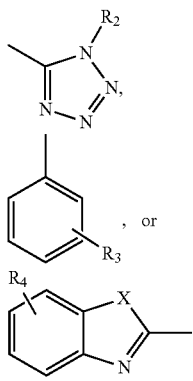

, or wherein:
R$_2$ is alkyl, aryl, arylalkyl or cycloalkyl,
R$_3$ is H, alkyl, aryl, arylalkyl, CF$_3$, halo or NO$_2$,
R$_4$ is H, alkyl, alkoxy, haloalkyl, monohaloalkyloxy, or dihaloalkyloxy, and
X is O, N—H, N-alkyl or S;
or reacting a compound of Formula-8

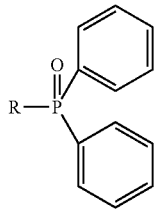

Formula-8 wherein R is defined as above and is linked to the phosphorus atom with a methylene group (—CH$_2$—);
or reacting a compound of Formula-9

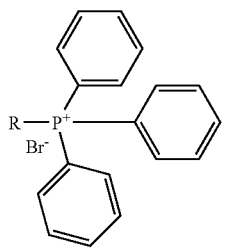

Formula-9 wherein R is defined as above and is linked to the phosphorus atom with a methylene group (—CH$_2$—), with a compound of Formula-3,

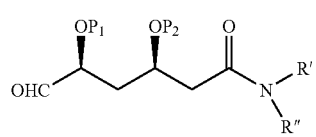

Formula-3 wherein:
P$_1$, P$_2$, R' and R" are defined as above,
in the presence of a base in a solvent, followed by isolating the compound of Formula-4 using hydrocarbon solvent to provide the compound of Formula-4.

2. A process for the preparation of a compound of Formula-4a',

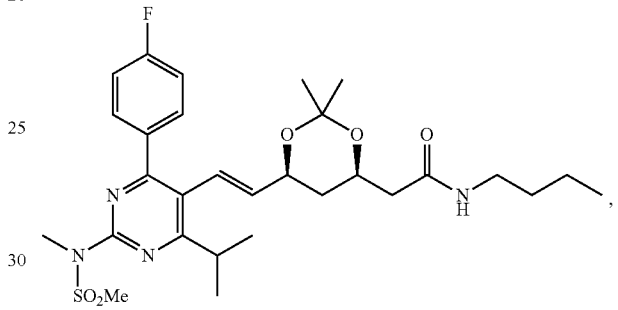

Formula-4a' the process comprising:
reacting a compound of Formula-2a

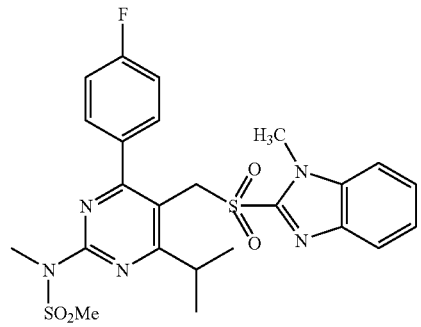

Formula-2a with a compound of Formula-3b

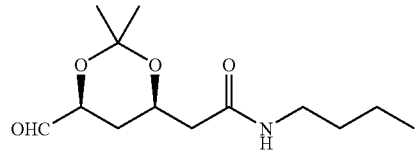

Formula-3b in the presence of an alkali metal carbonate in a polar aprotic solvent, then isolating the compound of Formula-4a' using a hydrocarbon solvent to provide the compound of Formula-4a'.

* * * * *